United States Patent [19]

Barrett et al.

[11] Patent Number: 5,635,597

[45] Date of Patent: Jun. 3, 1997

[54] PEPTIDES THAT BIND IL-2 RECEPTORS

[75] Inventors: Ronald W. Barrett, Sunnyvale; Tania Chernov-Rogan, Belmont; Ann M. Davis, Mountain View, all of Calif.

[73] Assignee: Affymax Technologies, N.V., Curacao, Netherlands Antilles

[21] Appl. No.: 250,789

[22] Filed: May 27, 1994

[51] Int. Cl.$^6$ .................................................. C07K 7/08
[52] U.S. Cl. .......................... 530/327; 530/300; 530/350; 530/351
[58] Field of Search ................... 530/300, 327, 530/350, 351

[56] References Cited

U.S. PATENT DOCUMENTS

| | | | |
|---|---|---|---|
| 4,931,544 | 6/1990 | Katre et al. | 530/351 |
| 5,198,359 | 3/1993 | Taniguchi et al. | 435/252.3 |
| 5,229,109 | 7/1993 | Grimm et al. | 424/85.2 |

FOREIGN PATENT DOCUMENTS

| | | |
|---|---|---|
| 0 319 012 | 6/1989 | European Pat. Off. |
| 0 539 748 A1 | 5/1993 | European Pat. Off. |
| 0 578 932 A2 | 1/1994 | European Pat. Off. |
| WO90/07861 | 7/1990 | WIPO |

OTHER PUBLICATIONS

Minami, Y. et al., "The IL–2 Receptor Complex: Its Structure, Function, and Target Genes", *Annu. Rev. Immunol.* 11:245–67.

Kondo, M. et al., "Sharing of the Interleukin-2 (IL–2) Receptor γ Chain Between Receptors for IL–2 and IL–4", *Science*, 262:1874–1876 (1993).

Zurawski, G., "Analysing lymphokine–receptor interactions of IL–1 and IL–2 by recombinant–DNA technology", *Tibtech*, 9:250–257 (1991).

Ballard, D.W. et al., "Structure of the Human Interleukin 2 Receptor and the Biochemical Basis for its Regulation", *The Molecular Aspects of Autoimmunity*, pp. 219–229 (1990).

Kundig, T.M. et al., "Immune Responses in Interleukin–2–Deficient Mice", *Science*, 262:1059–1061, (1993).

Van Brunt, J., "Cell Therapeutics Reports on IL–2 Signaling Pathway", *BioWorld Today*, p. 4 (1993).

Nowak, R., "'Bubble Boy' Paradox Resolved", *Science*, 262:1818 (1993).

Asinari, R., "Two unsung interleukins show renewed promise", *Biotechnology News*, 14(4):4–6 (1994).

Noguchi, M. et al., "Interleukin–2 Receptor γ Chain: A Functional Component of the Interleukin–7 Receptor", *Science* 262:1877–1880 (1993).

Russell, S.M. et al., "Interleukin–2 Receptor γ Chain: A Functional Component of the Interleukin–4 Receptor" *Science* 262:1880–1883 (1993).

Bowie et al. (1990) Science. vol. 247, pp. 1306–1310.

Devlin et al. (1990) Science vol. 249. pp. 404–406.

Leonard et al. (1984) Nature vol. 311, pp. 626–631.

*Primary Examiner*—John Ulm
*Assistant Examiner*—Prema Mertz
*Attorney, Agent, or Firm*—David P. Lentini; Lauren L. Stevens

[57] ABSTRACT

Peptides that bind to the Interleukin-2 (IL-2) receptor subunits IL-2Rα, IL-2Rβ and IL-2Rγ, and inhibit the binding of IL-2 to these important receptors, are described. The invention also includes methods for treating diseases related to the activation of these receptors, as well as the receptors for IL-4, -7 and -13. In addition, the present invention also includes methods for assaying for the presence of these receptors on cell surfaces.

37 Claims, No Drawings

SEQUENCE LISTING ( 1 ) GENERAL INFORMATION:

( i i i ) NUMBER OF SEQUENCES: 194

( 2 ) INFORMATION FOR SEQ ID NO:1:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Region
        ( B ) LOCATION: one-of(1-4)
        ( D ) OTHER INFORMATION: /note= "Xaa is any amino acid."

( i x ) FEATURE:
        ( A ) NAME/KEY: Region
        ( B ) LOCATION: one-of(13)
        ( D ) OTHER INFORMATION: /note= "Xaa is Val or Ile."

( i x ) FEATURE:
        ( A ) NAME/KEY: Region
        ( B ) LOCATION: one-of(14)
        ( D ) OTHER INFORMATION: /note= "Xaa is Pro, Val, Gly, Trp or Glu."

( x i ) SEQUENCE DESCRIPTION: SEQ ID NO:1:

Xaa Xaa Xaa Xaa Arg Trp Gly Asp Val Gly Asp Leu Xaa Xaa (2) INFORMATION FOR SEQ ID NO:2:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Region
        (B) LOCATION: one-of(1)
        (D) OTHER INFORMATION: /note= "Xaa is Ile, Gly or Phe."

(ix) FEATURE:
        (A) NAME/KEY: Region
        (B) LOCATION: one-of(2)
        (D) OTHER INFORMATION: /note= "Xaa is Ser, Val, or Pro."

(ix) FEATURE:
        (A) NAME/KEY: Region
        (B) LOCATION: one-of(3)
        (D) OTHER INFORMATION: /note= "Xaa is Ala, Gln or Val."

(ix) FEATURE:
        (A) NAME/KEY: Region
        (B) LOCATION: one-of(4)
        (D) OTHER INFORMATION: /note= "Xaa is Gly, Ser or Pro."

(ix) FEATURE:
        (A) NAME/KEY: Region
        (B) LOCATION: one-of(13)
        (D) OTHER INFORMATION: /note= "Xaa is Ile."

(ix) FEATURE:
        (A) NAME/KEY: Region
        (B) LOCATION: one-of(14)
        (D) OTHER INFORMATION: /note= "Xaa is Pro or Glu."

(ix) FEATURE:
        (A) NAME/KEY: Region
        (B) LOCATION: one-of(15)
        (D) OTHER INFORMATION: /note= "Xaa is Trp or Leu."

(xi) SEQUENCE DESCRIPTION: SEQ ID NO:2:

```
Xaa Xaa Xaa Xaa Arg Trp Gly Asp Val Gly Asp Leu Xaa Xaa Xaa
 1               5                  10                  15
```

(2) INFORMATION FOR SEQ ID NO:3:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Region
        (B) LOCATION: one-of(2)
        (D) OTHER INFORMATION: /note= "Xaa is Tyr or Trp."

(ix) FEATURE:
        (A) NAME/KEY: Region
        (B) LOCATION: one-of(4)
        (D) OTHER INFORMATION: /note= "Xaa is Asp or Glu."

(ix) FEATURE:
        (A) NAME/KEY: Region
        (B) LOCATION: one-of(8)
        (D) OTHER INFORMATION: /note= "Xaa is Leu or Met."

(ix) FEATURE:

(A) NAME/KEY: Region
(B) LOCATION: one-of(9)
(D) OTHER INFORMATION: /note= "Xaa is Val, Leu or Ile."

(ix) FEATURE:
(A) NAME/KEY: Region
(B) LOCATION: one-of(10)
(D) OTHER INFORMATION: /note= "Xaa is Pro, Gly, Val, Trp, Glu, Ala, Met or Ser."

(xi) SEQUENCE DESCRIPTION: SEQ ID NO:3:

Arg Xaa Glu Xaa Val Gly Asp Xaa Xaa Xaa
1               5                       10

(2) INFORMATION FOR SEQ ID NO:4:

(i) SEQUENCE CHARACTERISTICS:
(A) LENGTH: 10 amino acids
(B) TYPE: amino acid
(C) STRANDEDNESS: single
(D) TOPOLOGY: linear (ii) MOLECULE TYPE: peptide (ix) FEATURE:
(A) NAME/KEY: Region
(B) LOCATION: one-of(8)
(D) OTHER INFORMATION: /note= "Xaa is Asp or Gly."

(xi) SEQUENCE DESCRIPTION: SEQ ID NO:4:

Ser Gly Cys Gly Arg Glu Leu Xaa Trp Cys
1               5                       10

(2) INFORMATION FOR SEQ ID NO:5:

(i) SEQUENCE CHARACTERISTICS:
(A) LENGTH: 10 amino acids
(B) TYPE: amino acid
(C) STRANDEDNESS: single
(D) TOPOLOGY: linear (ii) MOLECULE TYPE: peptide (ix) FEATURE:
(A) NAME/KEY: Region
(B) LOCATION: one-of(2)
(D) OTHER INFORMATION: /note= "Xaa is Asp, Ser, Tyr or Glu."

(ix) FEATURE:
(A) NAME/KEY: Region
(B) LOCATION: one-of(6)
(D) OTHER INFORMATION: /note= "Xaa is Val or Leu."

(ix) FEATURE:
(A) NAME/KEY: Region
(B) LOCATION: one-of(9)
(D) OTHER INFORMATION: /note= "Xaa is Tyr or Phe."

(ix) FEATURE:
(A) NAME/KEY: Region
(B) LOCATION: one-of(10)
(D) OTHER INFORMATION: /note= "Xaa is Phe, Ile or Met."

(xi) SEQUENCE DESCRIPTION: SEQ ID NO:5:

Trp Xaa Gly Pro Gly Xaa Gly Glu Xaa Xaa
1               5                       10

(2) INFORMATION FOR SEQ ID NO:6:

(i) SEQUENCE CHARACTERISTICS:
(A) LENGTH: 12 amino acids
(B) TYPE: amino acid
(C) STRANDEDNESS: single
(D) TOPOLOGY: linear (i i) MOLECULE TYPE: peptide (x i) SEQUENCE DESCRIPTION: SEQ ID NO:6:

Met Asp Cys Ser Glu Ala Val Leu Gly Glu Leu Cys
1               5                   10

(2) INFORMATION FOR SEQ ID NO:7:

(i) SEQUENCE CHARACTERISTICS:
        (A) LENGTH: 12 amino acids
        (B) TYPE: amino acid
        (C) STRANDEDNESS: single
        (D) TOPOLOGY: linear (i i) MOLECULE TYPE: peptide (x i) SEQUENCE DESCRIPTION: SEQ ID NO:7:

His Cys Leu Asp Met Gly Cys Thr Phe Pro Val Trp
1               5                   10

(2) INFORMATION FOR SEQ ID NO:8:

(i) SEQUENCE CHARACTERISTICS:
        (A) LENGTH: 12 amino acids
        (B) TYPE: amino acid
        (C) STRANDEDNESS: single
        (D) TOPOLOGY: linear (i i) MOLECULE TYPE: peptide (x i) SEQUENCE DESCRIPTION: SEQ ID NO:8:

Ala Arg Ser Asp Tyr Gly Leu Gly Ala Ile Trp Pro
1               5                   10

(2) INFORMATION FOR SEQ ID NO:9:

(i) SEQUENCE CHARACTERISTICS:
        (A) LENGTH: 12 amino acids
        (B) TYPE: amino acid
        (C) STRANDEDNESS: single
        (D) TOPOLOGY: linear (i i) MOLECULE TYPE: peptide (x i) SEQUENCE DESCRIPTION: SEQ ID NO:9:

Arg Ala Cys Arg Val Met Pro Cys Leu Pro Asp Leu
1               5                   10

(2) INFORMATION FOR SEQ ID NO:10:

(i) SEQUENCE CHARACTERISTICS:
        (A) LENGTH: 12 amino acids
        (B) TYPE: amino acid
        (C) STRANDEDNESS: single
        (D) TOPOLOGY: linear (i i) MOLECULE TYPE: peptide (i x) FEATURE:
        (A) NAME/KEY: Region
        (B) LOCATION: one-of(1)
        (D) OTHER INFORMATION: /note= "Xaa is Met, Leu, Thr, Val or
            Ile."

(i x) FEATURE:
        (A) NAME/KEY: Region
        (B) LOCATION: one-of(2)
        (D) OTHER INFORMATION: /note= "Xaa is Asp, Asn, Gly, Glu or
            Ser."

(i x) FEATURE:

(A) NAME/KEY: Region
(B) LOCATION: one-of(3)
(D) OTHER INFORMATION: /note= "Xaa is Cys or Ser."

(ix) FEATURE:
(A) NAME/KEY: Region
(B) LOCATION: one-of(4)
(D) OTHER INFORMATION: /note= "Xaa is Gly, Ser, His, Arg, Trp or Tyr."

(ix) FEATURE:
(A) NAME/KEY: Region
(B) LOCATION: one-of(5)
(D) OTHER INFORMATION: /note= "Xaa is any amino acid."

(ix) FEATURE:
(A) NAME/KEY: Region
(B) LOCATION: one-of(6)
(D) OTHER INFORMATION: /note= "Xaa is Ala or Arg."

(ix) FEATURE:
(A) NAME/KEY: Region
(B) LOCATION: one-of(7)
(D) OTHER INFORMATION: /note= "Xaa is Thr, Ala, Gly, Val, Met, Ile or Ser."

(ix) FEATURE:
(A) NAME/KEY: Region
(B) LOCATION: one-of(8)
(D) OTHER INFORMATION: /note= "Xaa is Leu, Val or Ile."

(ix) FEATURE:
(A) NAME/KEY: Region
(B) LOCATION: one-of(9)
(D) OTHER INFORMATION: /note= "Xaa is Gly or Trp."

(ix) FEATURE:
(A) NAME/KEY: Region
(B) LOCATION: one-of(10)
(D) OTHER INFORMATION: /note= "Xaa is Glu, Gln or Asp."

(xi) SEQUENCE DESCRIPTION: SEQ ID NO:10:

```
Xaa  Xaa  Xaa  Xaa  Xaa  Xaa  Xaa  Xaa  Xaa  Xaa  Leu  Cys
 1                  5                            10
```

(2) INFORMATION FOR SEQ ID NO:11:

(i) SEQUENCE CHARACTERISTICS:
(A) LENGTH: 12 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:11:

```
Ile  Asp  Cys  Gly  Val  Ala  Thr  Val  Gly  Glu  Leu  Cys
 1                  5                            10
```

(2) INFORMATION FOR SEQ ID NO:12:

(i) SEQUENCE CHARACTERISTICS:
(A) LENGTH: 12 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:12:

```
Ile  Asp  Cys  Ser  Glu  Ala  Ala  Leu  Gly  Glu  Leu  Cys
 1                  5                            10
```

(2) INFORMATION FOR SEQ ID NO:13:

( i ) SEQUENCE CHARACTERISTICS:
    ( A ) LENGTH: 12 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:13:

```
Ile Ser Cys Ser Glu Ala Gly Leu Gly Glu Leu Cys
1               5                   10
```

( 2 ) INFORMATION FOR SEQ ID NO:14:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:14:

```
Ile Asn Cys Ser Glu Ala Val Ile Gly Gln Leu Cys
1               5                   10
```

( 2 ) INFORMATION FOR SEQ ID NO:15:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:15:

```
Ile Asp Cys Ser Gln Ala Met Leu Gly Glu Leu Cys
1               5                   10
```

( 2 ) INFORMATION FOR SEQ ID NO:16:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:16:

```
Ile Asp Cys Ser Asn Ala Val Val Gly Gln Leu Cys
1               5                   10
```

( 2 ) INFORMATION FOR SEQ ID NO:17:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:17:

```
Ile Asp Cys Ser Glu Ala Val Leu Gly Glu Leu Cys
1               5                   10
```

( 2 ) INFORMATION FOR SEQ ID NO:18:

( i ) SEQUENCE CHARACTERISTICS:
    ( A ) LENGTH: 12 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:18:

```
Ile Asp Cys Ser Ala Ala Gly Leu Gly Glu Leu Cys
1               5                   10
```

( 2 ) INFORMATION FOR SEQ ID NO:19:

( i ) SEQUENCE CHARACTERISTICS:
    ( A ) LENGTH: 12 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:19:

```
Ile Asp Cys Ser Glu Ala Ala Leu Gly Thr Leu Cys
1               5                   10
```

( 2 ) INFORMATION FOR SEQ ID NO:20:

( i ) SEQUENCE CHARACTERISTICS:
    ( A ) LENGTH: 12 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:20:

```
Leu Asp Cys Ser Asn Ala Gly Val Gly Asp Leu Cys
1               5                   10
```

( 2 ) INFORMATION FOR SEQ ID NO:21:

( i ) SEQUENCE CHARACTERISTICS:
    ( A ) LENGTH: 12 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:21:

```
Leu Asp Cys Ser Ile Ala Ala Leu Gly Glu Leu Cys
1               5                   10
```

( 2 ) INFORMATION FOR SEQ ID NO:22:

( i ) SEQUENCE CHARACTERISTICS:
    ( A ) LENGTH: 12 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:22:

```
Leu Asp Cys Ser Glu Ala Val Leu Gly Glu Leu Cys
1               5                   10
```

( 2 ) INFORMATION FOR SEQ ID NO:23:

( i ) SEQUENCE CHARACTERISTICS:
 ( A ) LENGTH: 12 amino acids
 ( B ) TYPE: amino acid
 ( C ) STRANDEDNESS: single
 ( D ) TOPOLOGY: linear ( i i ) MOLECULE TYPE: peptide ( x i ) SEQUENCE DESCRIPTION: SEQ ID NO:23:

Leu Asp Cys Ser Glu Ala Ile Leu Gly Gln Leu Cys
1               5                   10

( 2 ) INFORMATION FOR SEQ ID NO:24:

( i ) SEQUENCE CHARACTERISTICS:
 ( A ) LENGTH: 12 amino acids
 ( B ) TYPE: amino acid
 ( C ) STRANDEDNESS: single
 ( D ) TOPOLOGY: linear ( i i ) MOLECULE TYPE: peptide ( x i ) SEQUENCE DESCRIPTION: SEQ ID NO:24:

Leu Asp Cys His Leu Ala Val Leu Gly Glu Leu Cys
1               5                   10

( 2 ) INFORMATION FOR SEQ ID NO:25:

( i ) SEQUENCE CHARACTERISTICS:
 ( A ) LENGTH: 12 amino acids
 ( B ) TYPE: amino acid
 ( C ) STRANDEDNESS: single
 ( D ) TOPOLOGY: linear ( i i ) MOLECULE TYPE: peptide ( x i ) SEQUENCE DESCRIPTION: SEQ ID NO:25:

Leu Asp Cys Gly Glu Ala Ile Leu Gly Glu Leu Cys
1               5                   10

( 2 ) INFORMATION FOR SEQ ID NO:26:

( i ) SEQUENCE CHARACTERISTICS:
 ( A ) LENGTH: 12 amino acids
 ( B ) TYPE: amino acid
 ( C ) STRANDEDNESS: single
 ( D ) TOPOLOGY: linear ( i i ) MOLECULE TYPE: peptide ( x i ) SEQUENCE DESCRIPTION: SEQ ID NO:26:

Leu Asp Cys Ser Val Ala Val Leu Gly Glu Leu Cys
1               5                   10

( 2 ) INFORMATION FOR SEQ ID NO:27:

( i ) SEQUENCE CHARACTERISTICS:
 ( A ) LENGTH: 12 amino acids
 ( B ) TYPE: amino acid
 ( C ) STRANDEDNESS: single
 ( D ) TOPOLOGY: linear ( i i ) MOLECULE TYPE: peptide ( x i ) SEQUENCE DESCRIPTION: SEQ ID NO:27:

Leu Asp Cys Arg Asp Ala Val Leu Gly Glu Leu Cys
1               5                   10

( 2 ) INFORMATION FOR SEQ ID NO:28:

( i ) SEQUENCE CHARACTERISTICS:
   ( A ) LENGTH: 12 amino acids
   ( B ) TYPE: amino acid
   ( C ) STRANDEDNESS: single
   ( D ) TOPOLOGY: linear ( i i ) MOLECULE TYPE: peptide ( x i ) SEQUENCE DESCRIPTION: SEQ ID NO:28:

```
Leu Asp Cys Ser Glu Ala Val Leu Gly His Leu Cys
1               5                   10
```

( 2 ) INFORMATION FOR SEQ ID NO:29:

( i ) SEQUENCE CHARACTERISTICS:
      ( A ) LENGTH: 12 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:29:

```
Met Asp Cys Ser Glu Arg Ala Leu Gly Glu Leu Cys
1               5                   10
```

( 2 ) INFORMATION FOR SEQ ID NO:30:

( i ) SEQUENCE CHARACTERISTICS:
      ( A ) LENGTH: 12 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:30:

```
Met Asp Cys Ser Gln Ala Ala Leu Gly Asp Leu Cys
1               5                   10
```

( 2 ) INFORMATION FOR SEQ ID NO:31:

( i ) SEQUENCE CHARACTERISTICS:
      ( A ) LENGTH: 12 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:31:

```
Met Asp Cys Ser Gln Ala Gly Leu Cys Glu Leu Cys
1               5                   10
```

( 2 ) INFORMATION FOR SEQ ID NO:32:

( i ) SEQUENCE CHARACTERISTICS:
      ( A ) LENGTH: 12 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:32:

```
Met Asp Cys Ser Val Ala Val Leu Gly Asp Leu Cys
1               5                   10
```

( 2 ) INFORMATION FOR SEQ ID NO:33:

( i ) SEQUENCE CHARACTERISTICS:
    ( A ) LENGTH: 12 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:33:

Met Asp Cys Arg Glu Ala Ala Leu Gly Glu Leu Cys
1             5                   10

( 2 ) INFORMATION FOR SEQ ID NO:34:

( i ) SEQUENCE CHARACTERISTICS:
    ( A ) LENGTH: 12 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:34:

Met Asp Cys Ser Asp Ala Val Leu Gly Asp Leu Cys
1             5                   10

( 2 ) INFORMATION FOR SEQ ID NO:35:

( i ) SEQUENCE CHARACTERISTICS:
    ( A ) LENGTH: 12 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:35:

Met Asp Cys Trp Glu Ala Ala Leu Gly Glu Leu Cys
1             5                   10

( 2 ) INFORMATION FOR SEQ ID NO:36:

( i ) SEQUENCE CHARACTERISTICS:
    ( A ) LENGTH: 12 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:36:

Met Asp Cys His Glu Ala Ala Leu Gly His Leu Cys
1             5                   10

( 2 ) INFORMATION FOR SEQ ID NO:37:

( i ) SEQUENCE CHARACTERISTICS:
    ( A ) LENGTH: 12 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:37:

Met Asp Cys Ser Glu Ala Leu Leu Gly Glu Leu Cys
1             5                   10

( 2 ) INFORMATION FOR SEQ ID NO:38:

( i ) SEQUENCE CHARACTERISTICS:
    ( A ) LENGTH: 12 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:38:

Met Asp Cys Ser Gln Ala Val Leu Gly Glu Leu Cys
1               5                   10

( 2 ) INFORMATION FOR SEQ ID NO:39:

( i ) SEQUENCE CHARACTERISTICS:
    ( A ) LENGTH: 12 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:39:

Met Asp Cys Tyr Asp Ala Arg Leu Gly Asp Leu Cys
1               5                   10

( 2 ) INFORMATION FOR SEQ ID NO:40:

( i ) SEQUENCE CHARACTERISTICS:
    ( A ) LENGTH: 12 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:40:

Met Asp Cys Ser Ile Arg Ala Leu Gly Glu Leu Cys
1               5                   10

( 2 ) INFORMATION FOR SEQ ID NO:41:

( i ) SEQUENCE CHARACTERISTICS:
    ( A ) LENGTH: 12 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:41:

Met Asp Ser Ser Gln Ala Ala Leu Gly Glu Leu Cys
1               5                   10

( 2 ) INFORMATION FOR SEQ ID NO:42:

( i ) SEQUENCE CHARACTERISTICS:
    ( A ) LENGTH: 12 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:42:

Thr Glu Cys Ser Glu Ala Gly Leu Trp Glu Leu Cys
1               5                   10

( 2 ) INFORMATION FOR SEQ ID NO:43:

( i ) SEQUENCE CHARACTERISTICS:
- ( A ) LENGTH: 12 amino acids
- ( B ) TYPE: amino acid
- ( C ) STRANDEDNESS: single
- ( D ) TOPOLOGY: linear ( i i ) MOLECULE TYPE: peptide ( x i ) SEQUENCE DESCRIPTION: SEQ ID NO:43:

```
Val Asp Cys Ser Glu Ala Val Leu Gly Gln Leu Cys
1               5                   10
```

( 2 ) INFORMATION FOR SEQ ID NO:44:

( i ) SEQUENCE CHARACTERISTICS:
- ( A ) LENGTH: 12 amino acids
- ( B ) TYPE: amino acid
- ( C ) STRANDEDNESS: single
- ( D ) TOPOLOGY: linear ( i i ) MOLECULE TYPE: peptide ( x i ) SEQUENCE DESCRIPTION: SEQ ID NO:44:

```
Met Asp Cys Ser Glu Ala Val Leu Gly Glu Leu Cys
1               5                   10
```

( 2 ) INFORMATION FOR SEQ ID NO:45:

( i ) SEQUENCE CHARACTERISTICS:
- ( A ) LENGTH: 12 amino acids
- ( B ) TYPE: amino acid
- ( C ) STRANDEDNESS: single
- ( D ) TOPOLOGY: linear ( i i ) MOLECULE TYPE: peptide ( x i ) SEQUENCE DESCRIPTION: SEQ ID NO:45:

```
Ile Ser Cys Ser Glu Ala Gly Leu Gly Glu Leu Cys
1               5                   10
```

( 2 ) INFORMATION FOR SEQ ID NO:46:

( i ) SEQUENCE CHARACTERISTICS:
- ( A ) LENGTH: 12 amino acids
- ( B ) TYPE: amino acid
- ( C ) STRANDEDNESS: single
- ( D ) TOPOLOGY: linear ( i i ) MOLECULE TYPE: peptide ( x i ) SEQUENCE DESCRIPTION: SEQ ID NO:46:

```
Met Asp Cys Ser Glu Arg Ala Leu Gly Glu Leu Cys
1               5                   10
```

( 2 ) INFORMATION FOR SEQ ID NO:47:

( i ) SEQUENCE CHARACTERISTICS:
- ( A ) LENGTH: 12 amino acids
- ( B ) TYPE: amino acid
- ( C ) STRANDEDNESS: single
- ( D ) TOPOLOGY: linear ( i i ) MOLECULE TYPE: peptide ( x i ) SEQUENCE DESCRIPTION: SEQ ID NO:47:

```
Met Asp Cys Ser Gln Ala Ala Leu Gly Asp Leu Cys
1               5                   10
```

( 2 ) INFORMATION FOR SEQ ID NO:48:

(i) SEQUENCE CHARACTERISTICS:
      (A) LENGTH: 12 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:48:

Met Asp Cys Ser Gln Ala Gly Leu Gly Glu Leu Cys
1               5                   10

(2) INFORMATION FOR SEQ ID NO:49:

(i) SEQUENCE CHARACTERISTICS:
      (A) LENGTH: 16 amino acids
      (B) TYPE: amino acid
      (C) STRANDEDNESS: single
      (D) TOPOLOGY: linear (ii) MOLECULE TYPE: peptide (ix) FEATURE:
      (A) NAME/KEY: Region
      (B) LOCATION: one- of(1,3,5,6,7,10,13,15,16)
      (D) OTHER INFORMATION: /note= "Xaa is any amino acid."

(ix) FEATURE:
      (A) NAME/KEY: Region
      (B) LOCATION: one-of(2)
      (D) OTHER INFORMATION: /note= "Xaa is Val or Arg."

(xi) SEQUENCE DESCRIPTION: SEQ ID NO:49:

Xaa Xaa Xaa Cys Xaa Xaa Xaa Gly Cys Xaa Gly Ser Xaa Trp Xaa Xaa
1               5                   10                  15

(2) INFORMATION FOR SEQ ID NO:50:

(i) SEQUENCE CHARACTERISTICS:
      (A) LENGTH: 10 amino acids
      (B) TYPE: amino acid
      (C) STRANDEDNESS: single
      (D) TOPOLOGY: linear (ii) MOLECULE TYPE: peptide (ix) FEATURE:
      (A) NAME/KEY: Region
      (B) LOCATION: one-of(1)
      (D) OTHER INFORMATION: /note= "Xaa is Tyr, Phe, Leu or Trp."

(ix) FEATURE:
      (A) NAME/KEY: Region
      (B) LOCATION: one-of(2)
      (D) OTHER INFORMATION: /note= "Xaa is Val or Arg."

(ix) FEATURE:
      (A) NAME/KEY: Region
      (B) LOCATION: one-of(3)
      (D) OTHER INFORMATION: /note= "Xaa is Ala, Arg or Ile."

(ix) FEATURE:
      (A) NAME/KEY: Region
      (B) LOCATION: one- of(3,5,6,7,10)
      (D) OTHER INFORMATION: /note= "Xaa is any amino acid."

(xi) SEQUENCE DESCRIPTION: SEQ ID NO:50:

Xaa Xaa Xaa Cys Xaa Xaa Xaa Gly Cys Xaa
1               5                   10

(2) INFORMATION FOR SEQ ID NO:51:

(i) SEQUENCE CHARACTERISTICS:

(A) LENGTH: 16 amino acids
(B) TYPE: amino acid
(C) STRANDEDNESS: single
(D) TOPOLOGY: linear (ii) MOLECULE TYPE: peptide (ix) FEATURE:
(A) NAME/KEY: Region
(B) LOCATION: one-of(1)
(D) OTHER INFORMATION: /note= "Xaa is Tyr or Phe."

(ix) FEATURE:
(A) NAME/KEY: Region
(B) LOCATION: one-of(5)
(D) OTHER INFORMATION: /note= "Xaa is Ser, Gly, Ala, Asn or Thr."

(ix) FEATURE:
(A) NAME/KEY: Region
(B) LOCATION: one-of(6)
(D) OTHER INFORMATION: /note= "Xaa is an amino acid with acidic side chains."

(ix) FEATURE:
(A) NAME/KEY: Region
(B) LOCATION: one-of(7)
(D) OTHER INFORMATION: /note= "Xaa is Ser, Thr, Asn, Asp or Ile."

(ix) FEATURE:
(A) NAME/KEY: Region
(B) LOCATION: one-of(13)
(D) OTHER INFORMATION: /note= "Xaa is Ser or Thr."

(ix) FEATURE:
(A) NAME/KEY: Region
(B) LOCATION: one-of(15,16)
(D) OTHER INFORMATION: /note= "Xaa is any amino acid."

(xi) SEQUENCE DESCRIPTION: SEQ ID NO:51:

| Xaa | Val | Arg | Cys | Xaa | Xaa | Xaa | Gly | Cys | Val | Gly | Ser | Xaa | Trp | Xaa | Xaa |
|---|---|---|---|---|---|---|---|---|---|---|---|---|---|---|---|
| 1 | | | | 5 | | | | | 10 | | | | | 15 | |

(2) INFORMATION FOR SEQ ID NO:52:

(i) SEQUENCE CHARACTERISTICS:
(A) LENGTH: 16 amino acids
(B) TYPE: amino acid
(C) STRANDEDNESS: single
(D) TOPOLOGY: linear (ii) MOLECULE TYPE: peptide (ix) FEATURE:
(A) NAME/KEY: Region
(B) LOCATION: one-of(1)
(D) OTHER INFORMATION: /note= "Xaa is Tyr or Phe."

(ix) FEATURE:
(A) NAME/KEY: Region
(B) LOCATION: one-of(3)
(D) OTHER INFORMATION: /note= "Xaa is Arg, Leu or Ala."

(ix) FEATURE:
(A) NAME/KEY: Region
(B) LOCATION: one-of(4)
(D) OTHER INFORMATION: /note= "Xaa is Cys or Ser."

(ix) FEATURE:
(A) NAME/KEY: Region
(B) LOCATION: one-of(5)
(D) OTHER INFORMATION: /note= "Xaa is Ser, Thr or Gly."

(ix) FEATURE:
(A) NAME/KEY: Region
(B) LOCATION: one-of(6)
(D) OTHER INFORMATION: /note= "Xaa is Ala, Glu, Asp, Gln or ( i x ) FEATURE:
    ( A ) NAME/KEY: Region
    ( B ) LOCATION: one-of(7)
    ( D ) OTHER INFORMATION: /note= "Xaa is Asn, Ser, Thr, Asp, Leu, Ala or Ile."

( i x ) FEATURE:
    ( A ) NAME/KEY: Region
    ( B ) LOCATION: one-of(13)
    ( D ) OTHER INFORMATION: /note= "Xaa is Ser, Thr, Gly or Leu."

( i x ) FEATURE:
    ( A ) NAME/KEY: Region
    ( B ) LOCATION: one-of(15)
    ( D ) OTHER INFORMATION: /note= "Xaa is Val, Thr, Asn, His, Ser, Leu or Gly."

( i x ) FEATURE:
    ( A ) NAME/KEY: Region
    ( B ) LOCATION: one-of(16)
    ( D ) OTHER INFORMATION: /note= "Xaa is Phe, Tyr, Gly, His, Leu, Thr, Val, Ala or Ile."

( x i ) SEQUENCE DESCRIPTION: SEQ ID NO:52:

Xaa Val Xaa Xaa Xaa Xaa Xaa Gly Cys Val Gly Ser Xaa Trp Xaa Xaa
1               5                   10                  15

( 2 ) INFORMATION FOR SEQ ID NO:53:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Region
        ( B ) LOCATION: one-of(1)
        ( D ) OTHER INFORMATION: /note= "Xaa is Tyr or Phe."

( i x ) FEATURE:
        ( A ) NAME/KEY: Region
        ( B ) LOCATION: one-of(2,11)
        ( D ) OTHER INFORMATION: /note= "Xaa is Ser or Gly."

( i x ) FEATURE:
        ( A ) NAME/KEY: Region
        ( B ) LOCATION: one-of(7)
        ( D ) OTHER INFORMATION: /note= "Xaa is Ser, Arg, Ile, Gly or Asn."

( i x ) FEATURE:
        ( A ) NAME/KEY: Region
        ( B ) LOCATION: one-of(12)
        ( D ) OTHER INFORMATION: /note= "Xaa is Ser, His, Cys or Gln."

( i x ) FEATURE:
        ( A ) NAME/KEY: Region
        ( B ) LOCATION: one-of(13)
        ( D ) OTHER INFORMATION: /note= "Xaa is Phe, Glu, Ser, Arg, Asn, His or Thr."

( i x ) FEATURE:
        ( A ) NAME/KEY: Region
        ( B ) LOCATION: one-of(14)
        ( D ) OTHER INFORMATION: /note= "Xaa is Leu, Trp or Pro."

( i x ) FEATURE:
        ( A ) NAME/KEY: Region
        ( B ) LOCATION: one-of(15)
        ( D ) OTHER INFORMATION: /note= "Xaa is His, Val, Gly, Ser, Glu, Asn, Ala or Thr."

( i x ) FEATURE:

(A) NAME/KEY: Region
(B) LOCATION: one-of(16-20)
(D) OTHER INFORMATION: /note= "Xaa is any amino acid."

(x i) SEQUENCE DESCRIPTION: SEQ ID NO:53:

Xaa Val Arg Cys Xaa Glu Xaa Gly Cys Val Xaa Xaa Xaa Xaa Xaa Xaa
1               5                   10                  15

Xaa Xaa Xaa Xaa
         20

(2) INFORMATION FOR SEQ ID NO:54:

(i) SEQUENCE CHARACTERISTICS:
        (A) LENGTH: 20 amino acids
        (B) TYPE: amino acid
        (C) STRANDEDNESS: single
        (D) TOPOLOGY: linear (i i) MOLECULE TYPE: peptide (i x) FEATURE:
        (A) NAME/KEY: Region
        (B) LOCATION: one-of(12)
        (D) OTHER INFORMATION: /note= "Xaa is Ser or Cys."

(i x) FEATURE:
        (A) NAME/KEY: Region
        (B) LOCATION: one-of(13)
        (D) OTHER INFORMATION: /note= "Xaa is Ser or Glu."

(i x) FEATURE:
        (A) NAME/KEY: Region
        (B) LOCATION: one-of(14)
        (D) OTHER INFORMATION: /note= "Xaa is Trp or Leu."

(i x) FEATURE:
        (A) NAME/KEY: Region
        (B) LOCATION: one-of(15)
        (D) OTHER INFORMATION: /note= "Xaa is Gly or Val."

(i x) FEATURE:
        (A) NAME/KEY: Region
        (B) LOCATION: one-of(16)
        (D) OTHER INFORMATION: /note= "Xaa is Ala or Trp."

(i x) FEATURE:
        (A) NAME/KEY: Region
        (B) LOCATION: one-of(17)
        (D) OTHER INFORMATION: /note= "Xaa is Tyr or Val."

(i x) FEATURE:
        (A) NAME/KEY: Region
        (B) LOCATION: one-of(18)
        (D) OTHER INFORMATION: /note= "Xaa is Ala or Phe."

(i x) FEATURE:
        (A) NAME/KEY: Region
        (B) LOCATION: one-of(19)
        (D) OTHER INFORMATION: /note= "Xaa is Ser or Thr."

(i x) FEATURE:
        (A) NAME/KEY: Region
        (B) LOCATION: one-of(20)
        (D) OTHER INFORMATION: /note= "Xaa is Thr or Ile."

(x i) SEQUENCE DESCRIPTION: SEQ ID NO:54:

Tyr Val Arg Cys Ser Glu Ser Gly Cys Val Gly Xaa Xaa Xaa Xaa Xaa
1               5                   10                  15

Xaa Xaa Xaa Xaa
         20

(2) INFORMATION FOR SEQ ID NO:55:

(i) SEQUENCE CHARACTERISTICS:

(A) LENGTH: 10 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:55:

```
Cys Thr Gln Glu Val Tyr Tyr Ser Leu Leu
1               5                   10
```

(2) INFORMATION FOR SEQ ID NO:56:

(i) SEQUENCE CHARACTERISTICS:
   (A) LENGTH: 11 amino acids
   (B) TYPE: amino acid
   (C) STRANDEDNESS: single
   (D) TOPOLOGY: linear (ii) MOLECULE TYPE: peptide (xi) SEQUENCE DESCRIPTION: SEQ ID NO:56:

```
Cys Gly Thr Gln Glu Ala Cys Phe Gly Leu Leu
1               5                   10
```

(2) INFORMATION FOR SEQ ID NO:57:

(i) SEQUENCE CHARACTERISTICS:
   (A) LENGTH: 20 amino acids
   (B) TYPE: amino acid
   (C) STRANDEDNESS: single
   (D) TOPOLOGY: linear (ii) MOLECULE TYPE: peptide (ix) FEATURE:
   (A) NAME/KEY: Region
   (B) LOCATION: one-of(3)
   (D) OTHER INFORMATION: /note= "Xaa is Ala or Arg."

(ix) FEATURE:
   (A) NAME/KEY: Region
   (B) LOCATION: one-of(5)
   (D) OTHER INFORMATION: /note= "Xaa is Ser or Asn."

(ix) FEATURE:
   (A) NAME/KEY: Region
   (B) LOCATION: one-of(7)
   (D) OTHER INFORMATION: /note= "Xaa is Ser or Thr."

(ix) FEATURE:
   (A) NAME/KEY: Region
   (B) LOCATION: one-of(11)
   (D) OTHER INFORMATION: /note= "Xaa is Ser or Gly."

(ix) FEATURE:
   (A) NAME/KEY: Region
   (B) LOCATION: one-of(12)
   (D) OTHER INFORMATION: /note= "Xaa is Ser or Val."

(ix) FEATURE:
   (A) NAME/KEY: Region
   (B) LOCATION: one-of(13)
   (D) OTHER INFORMATION: /note= "Xaa is Thr, Asp or Ser."

(ix) FEATURE:
   (A) NAME/KEY: Region
   (B) LOCATION: one-of(14)
   (D) OTHER INFORMATION: /note= "Xaa is Ser or Trp."

(ix) FEATURE:
   (A) NAME/KEY: Region
   (B) LOCATION: one-of(15)
   (D) OTHER INFORMATION: /note= "Xaa is Ser, Leu or Ile."

(ix) FEATURE:

( A ) NAME/KEY: Region
                    ( B ) LOCATION: one-of(16)
                    ( D ) OTHER INFORMATION: /note= "Xaa is Ala or Phe."

( i x ) FEATURE:
                    ( A ) NAME/KEY: Region
                    ( B ) LOCATION: one-of(17)
                    ( D ) OTHER INFORMATION: /note= "Xaa is Gly, Asn or Ala."

( i x ) FEATURE:
                    ( A ) NAME/KEY: Region
                    ( B ) LOCATION: one-of(18)
                    ( D ) OTHER INFORMATION: /note= "Xaa is Ala, Pro or Gly."

( i x ) FEATURE:
                    ( A ) NAME/KEY: Region
                    ( B ) LOCATION: one-of(19)
                    ( D ) OTHER INFORMATION: /note= "Xaa is Leu, Trp or Pro."

( i x ) FEATURE:
                    ( A ) NAME/KEY: Region
                    ( B ) LOCATION: one-of(20)
                    ( D ) OTHER INFORMATION: /note= "Xaa is Phe or Gly."

( x i ) SEQUENCE DESCRIPTION: SEQ ID NO:57:

Tyr  Val  Xaa  Cys  Xaa  Glx  Xaa  Gly  Cys  Val  Xaa  Xaa  Xaa  Xaa  Xaa  Xaa
        1                   5                        10                       15

Xaa  Xaa  Xaa  Xaa
                        20

( 2 ) INFORMATION FOR SEQ ID NO:58:

( i ) SEQUENCE CHARACTERISTICS:
                    ( A ) LENGTH: 20 amino acids
                    ( B ) TYPE: amino acid
                    ( C ) STRANDEDNESS: single
                    ( D ) TOPOLOGY: linear ( i i ) MOLECULE TYPE: peptide ( x i ) SEQUENCE DESCRIPTION: SEQ ID NO:58:

Tyr  Val  Arg  Cys  Ser  Glu  Ser  Gly  Cys  Val  Gly  Ser  Thr  Trp  Leu  Phe
        1                   5                        10                       15

Asn  Pro  Trp  Gly
                        20

( 2 ) INFORMATION FOR SEQ ID NO:59:

( i ) SEQUENCE CHARACTERISTICS:
                    ( A ) LENGTH: 20 amino acids
                    ( B ) TYPE: amino acid
                    ( C ) STRANDEDNESS: single
                    ( D ) TOPOLOGY: linear ( i i ) MOLECULE TYPE: peptide ( x i ) SEQUENCE DESCRIPTION: SEQ ID NO:59:

Tyr  Val  Arg  Cys  Asn  Glu  Thr  Gly  Cys  Val  Gly  Ser  Ser  Trp  Ile  Ala
        1                   5                        10                       15

Ala  Gly  Pro  Phe
                        20

( 2 ) INFORMATION FOR SEQ ID NO:60:

( i ) SEQUENCE CHARACTERISTICS:
                    ( A ) LENGTH: 20 amino acids
                    ( B ) TYPE: amino acid
                    ( C ) STRANDEDNESS: single
                    ( D ) TOPOLOGY: linear ( i i ) MOLECULE TYPE: peptide ( x i ) SEQUENCE DESCRIPTION: SEQ ID NO:60:

Tyr Val Ala Cys Ser Glu Ser Gly Cys Val Ser Val Asp Ser Ser Ala
1               5                   10                  15

Gly Ala Leu Phe
            20

( 2 ) INFORMATION FOR SEQ ID NO:61:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Region
        ( B ) LOCATION: one-of(5)
        ( D ) OTHER INFORMATION: /note= "Xaa is Val, Glu or Asp."

( i x ) FEATURE:
        ( A ) NAME/KEY: Region
        ( B ) LOCATION: one-of(7)
        ( D ) OTHER INFORMATION: /note= "Xaa is Val or Ala."

( i i ) MOLECULE TYPE: peptide ( x i ) SEQUENCE DESCRIPTION: SEQ ID NO:61:

Arg Asp Cys Ser Xaa Ala Xaa Leu Gly Glu Leu Cys
1               5                   10

( 2 ) INFORMATION FOR SEQ ID NO:62:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:62:

Arg Asp Cys Ser Val Ala Val Leu Gly Glu Leu Cys
1               5                   10

( 2 ) INFORMATION FOR SEQ ID NO:63:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:63:

Arg Asp Cys Ser Glu Ala Arg Leu Gly Glu Leu Cys
1               5                   10

( 2 ) INFORMATION FOR SEQ ID NO:64:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:64:

Arg Asp Cys Ser Asp Ala Val Leu Gly Glu Leu Cys
1               5                   10

( 2 ) INFORMATION FOR SEQ ID NO:65:

( i ) SEQUENCE CHARACTERISTICS:
      ( A ) LENGTH: 10 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:65:

Ala Arg Gly Tyr Asp Val Gly Leu Ser Val
1               5                   10

( 2 ) INFORMATION FOR SEQ ID NO:66:

( i ) SEQUENCE CHARACTERISTICS:
      ( A ) LENGTH: 10 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:66:

Arg Trp Gly Asp Val Gly Asp Met Val Val
1               5                   10

( 2 ) INFORMATION FOR SEQ ID NO:67:

( i ) SEQUENCE CHARACTERISTICS:
      ( A ) LENGTH: 10 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:67:

Arg Tyr Gly Glu Val Gly Asp Leu Leu Pro
1               5                   10

( 2 ) INFORMATION FOR SEQ ID NO:68:

( i ) SEQUENCE CHARACTERISTICS:
      ( A ) LENGTH: 10 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:68:

Ser Gly Cys Gly Arg Glu Leu Asp Trp Cys
1               5                   10

( 2 ) INFORMATION FOR SEQ ID NO:69:

( i ) SEQUENCE CHARACTERISTICS:
      ( A ) LENGTH: 10 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:69:

Trp Asp Gly Pro Gly Leu Gly Glu Phe Phe
1               5                   10

( 2 ) INFORMATION FOR SEQ ID NO:70:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:70:

Xaa Xaa Xaa Xaa Gly Asp Met Val Val
1               5

( 2 ) INFORMATION FOR SEQ ID NO:71:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:71:

Arg Trp Gly Asp Val Xaa Xaa Xaa Xaa
1               5

( 2 ) INFORMATION FOR SEQ ID NO:72:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:72:

Xaa Xaa Xaa Xaa Arg Trp Gly Asp Val Gly Xaa Xaa Xaa Xaa
1               5                   10

( 2 ) INFORMATION FOR SEQ ID NO:73:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:73:

Ile Ser Ala Gly Arg Trp Gly Asp Val Gly Asp Leu Ile Pro
1               5                   10

( 2 ) INFORMATION FOR SEQ ID NO:74:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:74:

Phe Pro Val Pro Arg Trp Gly Asp Val Gly Asp Leu Ile Glu Leu
1               5                   10                  15

( 2 ) INFORMATION FOR SEQ ID NO:75:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:75:

Gly Val Gln Ser Arg Trp Gly Asp Val Gly Asp Leu Ile Pro Trp
1               5                   10                  15

( 2 ) INFORMATION FOR SEQ ID NO:76:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:76:

Arg Trp Gly Asp Val Gly Asp Leu Leu Pro
1               5                   10

( 2 ) INFORMATION FOR SEQ ID NO:77:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:77:

Arg Trp Gly Asp Val Gly Asp Leu Ile Gly
1               5                   10

( 2 ) INFORMATION FOR SEQ ID NO:78:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:78:

Arg Trp Gly Asp Val Gly Asp Leu Ile Trp
1               5                   10

( 2 ) INFORMATION FOR SEQ ID NO:79:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:79:

Arg Trp Gly Asp Val Gly Asp Leu Ile Val
1               5                   1 0

( 2 ) INFORMATION FOR SEQ ID NO:80:

( i ) SEQUENCE CHARACTERISTICS:
 ( A ) LENGTH: 10 amino acids
 ( B ) TYPE: amino acid
 ( C ) STRANDEDNESS: single
 ( D ) TOPOLOGY: linear ( i i ) MOLECULE TYPE: peptide ( x i ) SEQUENCE DESCRIPTION: SEQ ID NO:80:

Arg Trp Gly Asp Val Gly Asp Leu Val Ser
1               5                   1 0

( 2 ) INFORMATION FOR SEQ ID NO:81:

( i ) SEQUENCE CHARACTERISTICS:
 ( A ) LENGTH: 10 amino acids
 ( B ) TYPE: amino acid
 ( C ) STRANDEDNESS: single
 ( D ) TOPOLOGY: linear ( i i ) MOLECULE TYPE: peptide ( x i ) SEQUENCE DESCRIPTION: SEQ ID NO:81:

Arg Trp Gly Asp Val Gly Asp Leu Val Met
1               5                   1 0

( 2 ) INFORMATION FOR SEQ ID NO:82:

( i ) SEQUENCE CHARACTERISTICS:
 ( A ) LENGTH: 10 amino acids
 ( B ) TYPE: amino acid
 ( C ) STRANDEDNESS: single
 ( D ) TOPOLOGY: linear ( i i ) MOLECULE TYPE: peptide ( x i ) SEQUENCE DESCRIPTION: SEQ ID NO:82:

Arg Trp Gly Asp Val Gly Asp Met Val Glu
1               5                   1 0

( 2 ) INFORMATION FOR SEQ ID NO:83:

( i ) SEQUENCE CHARACTERISTICS:
 ( A ) LENGTH: 10 amino acids
 ( B ) TYPE: amino acid
 ( C ) STRANDEDNESS: single
 ( D ) TOPOLOGY: linear ( i i ) MOLECULE TYPE: peptide ( x i ) SEQUENCE DESCRIPTION: SEQ ID NO:83:

Arg Trp Gly Glu Val Gly Asp Leu Leu Pro
1               5                   1 0

( 2 ) INFORMATION FOR SEQ ID NO:84:

( i ) SEQUENCE CHARACTERISTICS:
 ( A ) LENGTH: 10 amino acids
 ( B ) TYPE: amino acid
 ( C ) STRANDEDNESS: single
 ( D ) TOPOLOGY: linear ( i i ) MOLECULE TYPE: peptide ( x i ) SEQUENCE DESCRIPTION: SEQ ID NO:84:

Arg Trp Gly Asp Val Gly Asp Leu Ile Pro
1               5                   10

( 2 ) INFORMATION FOR SEQ ID NO:85:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:85:

Arg Trp Gly Asp Val Gly Asp Leu Val Ala
1               5                   10

( 2 ) INFORMATION FOR SEQ ID NO:86:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:86:

Arg Trp Gly Asp Val Gly Asp Leu Val Glu
1               5                   10

( 2 ) INFORMATION FOR SEQ ID NO:87:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:87:

Arg Trp Gly Asp Val Gly Asp Leu Val Trp
1               5                   10

( 2 ) INFORMATION FOR SEQ ID NO:88:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:88:

Arg Trp Gly Asp Val Gly Asp Leu Val Gly
1               5                   10

( 2 ) INFORMATION FOR SEQ ID NO:89:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:89:

Arg Trp Gly Asp Val Gly Asp Leu Val Pro
1               5                   10

( 2 ) INFORMATION FOR SEQ ID NO:90:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:90:

Arg Trp Gly Asp Val Gly Asp Met Val Val
1               5                   10

( 2 ) INFORMATION FOR SEQ ID NO:91:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:91:

Ser Gly Cys Gly Arg Glu Leu Gly Trp Cys
1               5                   10

( 2 ) INFORMATION FOR SEQ ID NO:92:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:92:

Trp Asp Gly Pro Gly Leu Gly Glu Phe Phe
1               5                   10

( 2 ) INFORMATION FOR SEQ ID NO:93:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:93:

Trp Ser Gly Pro Gly Leu Gly Glu Phe Met
1               5                   10

( 2 ) INFORMATION FOR SEQ ID NO:94:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:94:

Trp Tyr Gly Pro Gly Leu Gly Glu Tyr Met
1               5                   10

( 2 ) INFORMATION FOR SEQ ID NO:95:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:95:

Trp Ser Gly Pro Gly Leu Gly Glu Tyr Met
1               5                   10

( 2 ) INFORMATION FOR SEQ ID NO:96:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:96:

Trp Glu Gly Pro Gly Leu Gly Glu Tyr Met
1               5                   10

( 2 ) INFORMATION FOR SEQ ID NO:97:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:97:

Trp Glu Gly Pro Gly Leu Gly Glu Tyr Ile
1               5                   10

( 2 ) INFORMATION FOR SEQ ID NO:98:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:98:

Phe Val Arg Cys Ser Ala Asn Gly Cys Val
1               5                   10

( 2 ) INFORMATION FOR SEQ ID NO:99:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:99:

Ile Asp Cys Ser Glu Ala Gly Leu Gly Glu Leu Cys
1               5                       10

( 2 ) INFORMATION FOR SEQ ID NO:100:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:100:

Met Asp Cys Arg Val Ala Ala Leu Gly Glu Leu Cys
1               5                       10

( 2 ) INFORMATION FOR SEQ ID NO:101:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:101:

Met Asp Cys Ser Lys Ala Ala Leu Gly Glu Leu Cys
1               5                       10

( 2 ) INFORMATION FOR SEQ ID NO:102:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:102:

Ser Val Arg Cys Ser Ala Ser Gly Cys Val
1               5                   10

( 2 ) INFORMATION FOR SEQ ID NO:103:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:103:

Glu Val Ile Cys Gly Thr Asp Gly Cys Trp
1               5                   10

( 2 ) INFORMATION FOR SEQ ID NO:104:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:104:

Tyr Val Ala Cys Ser Val Ser Gly Cys Val
1               5                   10

( 2 ) INFORMATION FOR SEQ ID NO:105:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:105:

Tyr Val Ile Cys Gly Ala Ser Gly Cys Val
1               5                   10

( 2 ) INFORMATION FOR SEQ ID NO:106:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:106:

Tyr Val Arg Cys Thr Ala Ile Gly Cys Val
1               5                   10

( 2 ) INFORMATION FOR SEQ ID NO:107:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:107:

Phe Val Arg Cys Ser Ala Thr Gly Cys Val
1               5                   10

( 2 ) INFORMATION FOR SEQ ID NO:108:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:108:

Tyr Val Ile Cys Ser Ala Ser Gly Cys Val
1               5                   10

( 2 ) INFORMATION FOR SEQ ID NO:109:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:109:

Trp Val Arg Cys Ser Ala Ser Gly Cys Val
1               5                    10

( 2 ) INFORMATION FOR SEQ ID NO:110:

( i ) SEQUENCE CHARACTERISTICS:
       ( A ) LENGTH: 10 amino acids
       ( B ) TYPE: amino acid
       ( C ) STRANDEDNESS: single
       ( D ) TOPOLOGY: linear ( i i ) MOLECULE TYPE: peptide ( x i ) SEQUENCE DESCRIPTION: SEQ ID NO:110:

Phe Val Arg Cys Ser Ala Ser Gly Cys Val
1               5                    10

( 2 ) INFORMATION FOR SEQ ID NO:111:

( i ) SEQUENCE CHARACTERISTICS:
       ( A ) LENGTH: 10 amino acids
       ( B ) TYPE: amino acid
       ( C ) STRANDEDNESS: single
       ( D ) TOPOLOGY: linear ( i i ) MOLECULE TYPE: peptide ( x i ) SEQUENCE DESCRIPTION: SEQ ID NO:111:

Phe Val Arg Cys Thr Ala Ser Gly Cys Val
1               5                    10

( 2 ) INFORMATION FOR SEQ ID NO:112:

( i ) SEQUENCE CHARACTERISTICS:
       ( A ) LENGTH: 10 amino acids
       ( B ) TYPE: amino acid
       ( C ) STRANDEDNESS: single
       ( D ) TOPOLOGY: linear ( i i ) MOLECULE TYPE: peptide ( x i ) SEQUENCE DESCRIPTION: SEQ ID NO:112:

Phe Val Arg Cys Thr Ser Asp Gly Cys Val
1               5                    10

( 2 ) INFORMATION FOR SEQ ID NO:113:

( i ) SEQUENCE CHARACTERISTICS:
       ( A ) LENGTH: 10 amino acids
       ( B ) TYPE: amino acid
       ( C ) STRANDEDNESS: single
       ( D ) TOPOLOGY: linear ( i i ) MOLECULE TYPE: peptide ( x i ) SEQUENCE DESCRIPTION: SEQ ID NO:113:

Tyr Val Arg Cys Thr Ala Ser Gly Cys Val
1               5                    10

( 2 ) INFORMATION FOR SEQ ID NO:114:

( i ) SEQUENCE CHARACTERISTICS:
       ( A ) LENGTH: 10 amino acids
       ( B ) TYPE: amino acid
       ( C ) STRANDEDNESS: single
       ( D ) TOPOLOGY: linear ( i i ) MOLECULE TYPE: peptide ( x i ) SEQUENCE DESCRIPTION: SEQ ID NO:114:

Phe Arg Arg Cys Ser Ala Ser Gly Cys Val
1               5                   10

( 2 ) INFORMATION FOR SEQ ID NO:115:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:115:

Leu Asp Cys Ser Arg Ala Ser Leu Gly Glu Leu Cys
1               5                   10

( 2 ) INFORMATION FOR SEQ ID NO:116:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:116:

Leu Arg Arg Cys Ser Ala Asn Gly Cys Val
1               5                   10

( 2 ) INFORMATION FOR SEQ ID NO:117:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:117:

Phe Val Arg Cys Ser Leu Ile Gly Cys Val
1               5                   10

( 2 ) INFORMATION FOR SEQ ID NO:118:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:118:

Phe Val Arg Cys Asn Ala Ser Gly Cys Val
1               5                   10

( 2 ) INFORMATION FOR SEQ ID NO:119:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:119:

Phe Val Arg Cys Thr Glu Trp Gly Cys Val
1               5                   10

( 2 ) INFORMATION FOR SEQ ID NO:120:

( i ) SEQUENCE CHARACTERISTICS:
       ( A ) LENGTH: 10 amino acids
       ( B ) TYPE: amino acid
       ( C ) STRANDEDNESS: single
       ( D ) TOPOLOGY: linear ( i i ) MOLECULE TYPE: peptide ( x i ) SEQUENCE DESCRIPTION: SEQ ID NO:120:

Phe Val Arg Cys Thr Ser Asp Gly Cys Val
1               5                   10

( 2 ) INFORMATION FOR SEQ ID NO:121:

( i ) SEQUENCE CHARACTERISTICS:
       ( A ) LENGTH: 10 amino acids
       ( B ) TYPE: amino acid
       ( C ) STRANDEDNESS: single
       ( D ) TOPOLOGY: linear ( i i ) MOLECULE TYPE: peptide ( x i ) SEQUENCE DESCRIPTION: SEQ ID NO:121:

Tyr Val Ile Cys Ser Ala Ser Gly Cys Val
1               5                   10

( 2 ) INFORMATION FOR SEQ ID NO:122:

( i ) SEQUENCE CHARACTERISTICS:
       ( A ) LENGTH: 10 amino acids
       ( B ) TYPE: amino acid
       ( C ) STRANDEDNESS: single
       ( D ) TOPOLOGY: linear ( i i ) MOLECULE TYPE: peptide ( x i ) SEQUENCE DESCRIPTION: SEQ ID NO:122:

Phe Val Arg Cys Ser Ala Asn Gly Cys Val
1               5                   10

( 2 ) INFORMATION FOR SEQ ID NO:123:

( i ) SEQUENCE CHARACTERISTICS:
       ( A ) LENGTH: 10 amino acids
       ( B ) TYPE: amino acid
       ( C ) STRANDEDNESS: single
       ( D ) TOPOLOGY: linear ( i i ) MOLECULE TYPE: peptide ( x i ) SEQUENCE DESCRIPTION: SEQ ID NO:123:

Phe Val Arg Cys Thr Ala Ser Gly Cys Ile
1               5                   10

( 2 ) INFORMATION FOR SEQ ID NO:124:

( i ) SEQUENCE CHARACTERISTICS:
       ( A ) LENGTH: 16 amino acids
       ( B ) TYPE: amino acid
       ( C ) STRANDEDNESS: single
       ( D ) TOPOLOGY: linear ( i i ) MOLECULE TYPE: peptide ( i x ) FEATURE:
  ( A ) NAME/KEY: Region
  ( B ) LOCATION: one- of(1,2,3,14,15,16)
  ( D ) OTHER INFORMATION: /note= "Xaa is any amino acid."

( i x ) FEATURE:
  ( A ) NAME/KEY: Region
  ( B ) LOCATION: one-of(4)
  ( D ) OTHER INFORMATION: /note= "Xaa is Tyr or Phe."

( x i ) SEQUENCE DESCRIPTION: SEQ ID NO:124:

```
Xaa Xaa Xaa Xaa Val Arg Cys Ser Ala Ser Gly Cys Val Xaa Xaa Xaa
1               5                   10                  15
```

( 2 ) INFORMATION FOR SEQ ID NO:125:

( i ) SEQUENCE CHARACTERISTICS:
  ( A ) LENGTH: 6 amino acids
  ( B ) TYPE: amino acid
  ( C ) STRANDEDNESS: single
  ( D ) TOPOLOGY: linear ( i i ) MOLECULE TYPE: peptide ( i x ) FEATURE:
  ( A ) NAME/KEY: Region
  ( B ) LOCATION: one-of(3)
  ( D ) OTHER INFORMATION: /note= "Xaa is Ser or Thr."

( x i ) SEQUENCE DESCRIPTION: SEQ ID NO:125:

```
Gly Ser Xaa Trp Xaa Xaa
1               5
```

( 2 ) INFORMATION FOR SEQ ID NO:126:

( i ) SEQUENCE CHARACTERISTICS:
  ( A ) LENGTH: 16 amino acids
  ( B ) TYPE: amino acid
  ( C ) STRANDEDNESS: single
  ( D ) TOPOLOGY: linear ( i i ) MOLECULE TYPE: peptide ( x i ) SEQUENCE DESCRIPTION: SEQ ID NO:126:

```
Tyr Val Arg Cys Ser Glu Ser Gly Cys Val Gly Ser Ser Trp Asn Ala
1               5                   10                  15
```

( 2 ) INFORMATION FOR SEQ ID NO:127:

( i ) SEQUENCE CHARACTERISTICS:
  ( A ) LENGTH: 16 amino acids
  ( B ) TYPE: amino acid
  ( C ) STRANDEDNESS: single
  ( D ) TOPOLOGY: linear ( i i ) MOLECULE TYPE: peptide ( x i ) SEQUENCE DESCRIPTION: SEQ ID NO:127:

```
Phe Val Arg Cys Ser Glu Ser Gly Cys Val Gly Ser Ser Trp Ser Ala
1               5                   10                  15
```

( 2 ) INFORMATION FOR SEQ ID NO:128:

( i ) SEQUENCE CHARACTERISTICS:
  ( A ) LENGTH: 16 amino acids
  ( B ) TYPE: amino acid
  ( C ) STRANDEDNESS: single
  ( D ) TOPOLOGY: linear ( i i ) MOLECULE TYPE: peptide ( x i ) SEQUENCE DESCRIPTION: SEQ ID NO:128:

```
Tyr Val Arg Cys Ser Ala Ser Gly Cys Val Gly Ser Ser Trp Phe Leu
1               5                   10                  15
```

( 2 ) INFORMATION FOR SEQ ID NO:129:

( i ) SEQUENCE CHARACTERISTICS:
        ( A ) LENGTH: 16 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:129:

```
Tyr Val Arg Cys Ser Asp Ser Gly Cys Val Gly Ser Thr Trp Gly Trp
1               5                   10                  15
```

( 2 ) INFORMATION FOR SEQ ID NO:130:

( i ) SEQUENCE CHARACTERISTICS:
        ( A ) LENGTH: 16 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:130:

```
Tyr Val Arg Cys Ser Glu Ser Gly Cys Val Gly Ser Thr Trp Val Phe
1               5                   10                  15
```

( 2 ) INFORMATION FOR SEQ ID NO:131:

( i ) SEQUENCE CHARACTERISTICS:
        ( A ) LENGTH: 16 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:131:

```
Tyr Val Arg Cys Ser Glu Ser Gly Cys Val Gly Ser Thr Trp Thr Phe
1               5                   10                  15
```

( 2 ) INFORMATION FOR SEQ ID NO:132:

( i ) SEQUENCE CHARACTERISTICS:
        ( A ) LENGTH: 16 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:132:

```
Tyr Val Leu Cys Ala Leu Ser Gly Cys Val Gly Ser Ser Trp Ser Ser
1               5                   10                  15
```

( 2 ) INFORMATION FOR SEQ ID NO:133:

( i ) SEQUENCE CHARACTERISTICS:
        ( A ) LENGTH: 16 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:133:

```
Tyr Val Arg Cys Gly Glu Ser Gly Cys Val Gly Ser Thr Trp Ser Thr
1               5                   10                  15
```

(2) INFORMATION FOR SEQ ID NO:134:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:134:

```
Tyr Val Arg Cys Ser Ala Thr Gly Cys Val Gly Ser Thr Trp Thr Phe
1               5                   10                  15
```

(2) INFORMATION FOR SEQ ID NO:135:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:135:

```
Tyr Val Arg Cys Gly Glu Thr Gly Cys Val Gly Ser Thr Trp Ser Phe
1               5                   10                  15
```

(2) INFORMATION FOR SEQ ID NO:136:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:136:

```
Tyr Val Arg Cys Gly Val Ser Gly Cys Val Gly Ser Ser Trp Val Leu
1               5                   10                  15
```

(2) INFORMATION FOR SEQ ID NO:137:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:137:

```
Tyr Val Arg Cys Gly Glu Ser Gly Cys Val Gly Ser Thr Trp Ser Thr
1               5                   10                  15
```

(2) INFORMATION FOR SEQ ID NO:138:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:138:

```
Phe Val Arg Cys Ser Glu Ser Gly Cys Val Gly Ser Ser Trp Ser Thr
1               5                   10                  15
```

(2) INFORMATION FOR SEQ ID NO:139:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:139:

```
Tyr Val Arg Cys Ser Glu Ser Gly Cys Val Gly Ser Ser Trp Trp Ala
1               5                   10                  15
```

(2) INFORMATION FOR SEQ ID NO:140:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:140:

```
Tyr Val Arg Cys Ser Ala Asn Gly Cys Val Gly Ser Ser Trp Val Phe
1               5                   10                  15
```

(2) INFORMATION FOR SEQ ID NO:141:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:141:

```
Tyr Val Arg Cys Ser Val Thr Gly Cys Val Gly Ser Ser Trp Ser Ile
1               5                   10                  15
```

(2) INFORMATION FOR SEQ ID NO:142:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:142:

```
Tyr Val Arg Cys Ser Glu Ser Gly Cys Val Gly Ser Ser Trp Ser Val
1               5                   10                  15
```

(2) INFORMATION FOR SEQ ID NO:143:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:143:

```
Phe Val Arg Cys Ser Ala Asp Gly Cys Val Gly Ser Ser Trp Leu Gln
1               5                   10                  15
```

( 2 ) INFORMATION FOR SEQ ID NO:144:

( i ) SEQUENCE CHARACTERISTICS:
        ( A ) LENGTH: 16 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:144:

```
Tyr Val Arg Cys Ser Ala Asp Gly Cys Val Gly Ser Ser Trp Phe Thr
1               5                   10                  15
```

( 2 ) INFORMATION FOR SEQ ID NO:145:

( i ) SEQUENCE CHARACTERISTICS:
        ( A ) LENGTH: 16 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:145:

```
Tyr Val Arg Cys Asn Pro Ser Gly Cys Val Gly Ser Ser Trp Ser Ile
1               5                   10                  15
```

( 2 ) INFORMATION FOR SEQ ID NO:146:

( i ) SEQUENCE CHARACTERISTICS:
        ( A ) LENGTH: 16 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:146:

```
Tyr Val Arg Cys Ser Val Thr Gly Cys Val Gly Ser Ser Trp Ser Ile
1               5                   10                  15
```

( 2 ) INFORMATION FOR SEQ ID NO:147:

( i ) SEQUENCE CHARACTERISTICS:
        ( A ) LENGTH: 16 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:147:

```
Tyr Val Arg Cys Ser Glu Ser Gly Cys Val Gly Ser Ser Trp Ser Val
1               5                   10                  15
```

( 2 ) INFORMATION FOR SEQ ID NO:148:

( i ) SEQUENCE CHARACTERISTICS:
        ( A ) LENGTH: 16 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:148:

Phe Val Arg Cys Ser Ala Asn Gly Cys Val Gly Ser Thr Trp Gln Ala
1               5                   10                  15

( 2 ) INFORMATION FOR SEQ ID NO:149:

( i ) SEQUENCE CHARACTERISTICS:
       ( A ) LENGTH: 16 amino acids
       ( B ) TYPE: amino acid
       ( C ) STRANDEDNESS: single
       ( D ) TOPOLOGY: linear ( i i ) MOLECULE TYPE: peptide ( x i ) SEQUENCE DESCRIPTION: SEQ ID NO:149:

Tyr Val Arg Cys Thr Glu Ser Gly Cys Val Gly Ser Thr Trp Thr Tyr
1               5                   10                  15

( 2 ) INFORMATION FOR SEQ ID NO:150:

( i ) SEQUENCE CHARACTERISTICS:
       ( A ) LENGTH: 16 amino acids
       ( B ) TYPE: amino acid
       ( C ) STRANDEDNESS: single
       ( D ) TOPOLOGY: linear ( i i ) MOLECULE TYPE: peptide ( x i ) SEQUENCE DESCRIPTION: SEQ ID NO:150:

Tyr Val Arg Cys Ser Val Thr Gly Cys Val Gly Ser Thr Trp Ser Val
1               5                   10                  15

( 2 ) INFORMATION FOR SEQ ID NO:151:

( i ) SEQUENCE CHARACTERISTICS:
       ( A ) LENGTH: 16 amino acids
       ( B ) TYPE: amino acid
       ( C ) STRANDEDNESS: single
       ( D ) TOPOLOGY: linear ( i i ) MOLECULE TYPE: peptide ( x i ) SEQUENCE DESCRIPTION: SEQ ID NO:151:

Tyr Val Arg Cys Ser Glu Ile Gly Cys Val Gly Ser Thr Trp Ser Leu
1               5                   10                  15

( 2 ) INFORMATION FOR SEQ ID NO:152:

( i ) SEQUENCE CHARACTERISTICS:
       ( A ) LENGTH: 16 amino acids
       ( B ) TYPE: amino acid
       ( C ) STRANDEDNESS: single
       ( D ) TOPOLOGY: linear ( i i ) MOLECULE TYPE: peptide ( x i ) SEQUENCE DESCRIPTION: SEQ ID NO:152:

Tyr Val Arg Cys Ser Ala Asn Gly Cys Val Gly Ser Ser Trp Val Phe
1               5                   10                  15

( 2 ) INFORMATION FOR SEQ ID NO:153:

( i ) SEQUENCE CHARACTERISTICS:
       ( A ) LENGTH: 16 amino acids
       ( B ) TYPE: amino acid
       ( C ) STRANDEDNESS: single
       ( D ) TOPOLOGY: linear ( i i ) MOLECULE TYPE: peptide ( x i ) SEQUENCE DESCRIPTION: SEQ ID NO:153:

Tyr Val Arg Cys Ser Ala Thr Gly Cys Val Gly Ser Ser Trp Val Gly
1               5                   10                  15

(2) INFORMATION FOR SEQ ID NO:154:

(i) SEQUENCE CHARACTERISTICS:
      (A) LENGTH: 16 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:154:

Phe Val Arg Cys Ser Ala Ser Gly Cys Val Gly Ser Ser Trp Val His
1               5                   10                  15

(2) INFORMATION FOR SEQ ID NO:155:

(i) SEQUENCE CHARACTERISTICS:
      (A) LENGTH: 16 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:155:

Tyr Val Arg Cys Ser Ala Asp Gly Cys Val Gly Ser Thr Trp Asn Leu
1               5                   10                  15

(2) INFORMATION FOR SEQ ID NO:156:

(i) SEQUENCE CHARACTERISTICS:
      (A) LENGTH: 16 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:156:

Tyr Val Arg Ser Ser Gln Ser Gly Cys Val Gly Ser Gly Trp Val Leu
1               5                   10                  15

(2) INFORMATION FOR SEQ ID NO:157:

(i) SEQUENCE CHARACTERISTICS:
      (A) LENGTH: 16 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:157:

Tyr Val Ala Cys Ser Glu Ser Gly Cys Val Gly Ser Ser Trp Ser Val
1               5                   10                  15

(2) INFORMATION FOR SEQ ID NO:158:

(i) SEQUENCE CHARACTERISTICS:
      (A) LENGTH: 16 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:158:

```
Phe Val Ala Cys Gly Glu Leu Gly Cys Val Gly Ser Ser Trp Ser Ile
1               5                   10                  15
```

( 2 ) INFORMATION FOR SEQ ID NO:159:

( i ) SEQUENCE CHARACTERISTICS:
        ( A ) LENGTH: 16 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:159:

```
Tyr Val Ala Cys Ser Glu Ser Gly Cys Val Gly Ser Ser Trp Leu Ala
1               5                   10                  15
```

( 2 ) INFORMATION FOR SEQ ID NO:160:

( i ) SEQUENCE CHARACTERISTICS:
        ( A ) LENGTH: 16 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:160:

```
Tyr Cys Arg Cys Thr Glu Ser Gly Cys Val Gly Ser Thr Trp Thr Tyr
1               5                   10                  15
```

( 2 ) INFORMATION FOR SEQ ID NO:161:

( i ) SEQUENCE CHARACTERISTICS:
        ( A ) LENGTH: 16 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:161:

```
Phe Val Arg Cys Thr Ala Ile Gly Cys Val Gly Ser Ser Trp Ser Val
1               5                   10                  15
```

( 2 ) INFORMATION FOR SEQ ID NO:162:

( i ) SEQUENCE CHARACTERISTICS:
        ( A ) LENGTH: 16 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:162:

```
Tyr Val Arg Cys Ser Ala Asp Gly Cys Val Gly Ser Ser Trp Ser Ala
1               5                   10                  15
```

( 2 ) INFORMATION FOR SEQ ID NO:163:

( i ) SEQUENCE CHARACTERISTICS:
        ( A ) LENGTH: 16 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:163:

```
Tyr Val Arg Cys Ser Ala Ser Gly Cys Val Gly Ser Ser Trp Asn Tyr
1               5                   10                  15
```

(2) INFORMATION FOR SEQ ID NO:164:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:164:

```
Tyr Val Leu Cys Ser Ala Ser Gly Cys Val Gly Ser Leu Trp Thr His
1               5                   10                  15
```

(2) INFORMATION FOR SEQ ID NO:165:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:165:

```
Tyr Val Arg Cys Thr Asp Ser Gly Cys Val Gly Ser Ser Trp His Leu
1               5                   10                  15
```

(2) INFORMATION FOR SEQ ID NO:166:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:166:

```
Tyr Val Ala Cys Ser Glu Ser Gly Cys Val Gly Ser Thr Trp Thr Thr
1               5                   10                  15
```

(2) INFORMATION FOR SEQ ID NO:167:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:167:

```
Tyr Val Ala Cys Ser Glu Ser Gly Cys Val Gly Ser Thr Trp Thr Phe
1               5                   10                  15
```

(2) INFORMATION FOR SEQ ID NO:168:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:168:

```
Tyr Val Arg Cys Gly Ala Ala Gly Cys Val Gly Ser Ser Trp Val Tyr
1               5                   10                  15
```

(2) INFORMATION FOR SEQ ID NO:169:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:169:

```
Phe Val Arg Cys Gly Ala Ser Gly Cys Val Gly Ser Thr Trp Gly Ser
1               5                   10                  15
```

(2) INFORMATION FOR SEQ ID NO:170:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:170:

```
Tyr Val Ala Cys Ser Glu Ile Gly Cys Val Gly Ser Thr Trp Ser Leu
1               5                   10                  15
```

(2) INFORMATION FOR SEQ ID NO:171:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:171:

```
Tyr Val Ala Cys Ser Glu Ser Gly Cys Val Gly Ser Ser Trp Thr Val
1               5                   10                  15
```

(2) INFORMATION FOR SEQ ID NO:172:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:172:

```
Tyr Val Ala Cys Ser Val Ser Gly Cys Val Gly Ser Ser Trp Ser Val
1               5                   10                  15
```

(2) INFORMATION FOR SEQ ID NO:173:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:173:

```
Tyr Val Arg Cys Ser Glu Ser Gly Cys Val Gly Ser Thr Trp Thr Thr
1               5                   10                  15
```

( 2 ) INFORMATION FOR SEQ ID NO:174:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:174:

```
Tyr Val Arg Cys Ser Glu Ser Gly Cys Val Xaa Xaa Xaa Xaa Xaa Xaa
1               5                   10                  15

Xaa Xaa Xaa Xaa
            20
```

( 2 ) INFORMATION FOR SEQ ID NO:175:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:175:

```
Tyr Val Arg Cys Ser Glu Ser Gly Cys Val Ser Ser Phe Trp Ser Ala
1               5                   10                  15

Pro Trp Lys Ala
            20
```

( 2 ) INFORMATION FOR SEQ ID NO:176:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:176:

```
Tyr Val Arg Cys Ser Glu Asn Gly Cys Val Ser His Ser Trp Thr Gln
1               5                   10                  15

Gly Leu Arg Thr
            20
```

( 2 ) INFORMATION FOR SEQ ID NO:177:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:177:

```
Tyr Val Arg Cys Ser Glu Ser Gly Cys Val Ser Gln Arg Pro His Val
1               5                   10                  15

Leu Glu Val Trp
            20
```

( 2 ) INFORMATION FOR SEQ ID NO:178:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:178:

```
Tyr Val Leu Cys Ser Glu Arg Gly Cys Val Gly Gln Asn Trp Ala Val
 1               5                  10                  15

Gly Lys Leu Pro
            20
```

( 2 ) INFORMATION FOR SEQ ID NO:179:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:179:

```
Tyr Val Arg Cys Ser Glu Ile Gly Cys Val Gly Ser His Trp Ser Ser
 1               5                  10                  15

Tyr Gly Lys His
            20
```

( 2 ) INFORMATION FOR SEQ ID NO:180:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:180:

```
Tyr Val Arg Cys Ser Glu Asn Gly Cys Val Gly Ser Ser Trp Gly Arg
 1               5                  10                  15

Val Thr Leu Asp
            20
```

( 2 ) INFORMATION FOR SEQ ID NO:181:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:181:

```
Tyr Val Arg Cys Ser Glu Ser Gly Cys Val Gly Ser Asn Trp Ser Gly
 1               5                  10                  15

Thr Leu Thr Thr
            20
```

( 2 ) INFORMATION FOR SEQ ID NO:182:

( i ) SEQUENCE CHARACTERISTICS:

(A) LENGTH: 20 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:182:

```
Tyr Val Arg Cys Ser Glu Ser Gly Cys Val Gly Ser Ser Trp Gly Ala
1               5                   10                  15
Val Ala Ser Ile
            20
```

(2) INFORMATION FOR SEQ ID NO:183:

(i) SEQUENCE CHARACTERISTICS:
(A) LENGTH: 20 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:183:

```
Tyr Val Arg Cys Ser Glu Ser Gly Cys Val Gly Cys Glu Leu Val Trp
1               5                   10                  15
Tyr Phe Thr Thr
            20
```

(2) INFORMATION FOR SEQ ID NO:184:

(i) SEQUENCE CHARACTERISTICS:
(A) LENGTH: 20 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:184:

```
Tyr Val Arg Cys Ser Glu Ser Gly Cys Val Gly Ser Ser Trp Ser Val
1               5                   10                  15
Ser Pro His Gly
            20
```

(2) INFORMATION FOR SEQ ID NO:185:

(i) SEQUENCE CHARACTERISTICS:
(A) LENGTH: 20 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:185:

```
Tyr Val Arg Cys Gly Glu Ser Gly Cys Val Ser Ser Ser Trp Ser Thr
1               5                   10                  15
Met Gly Asn Ser
            20
```

(2) INFORMATION FOR SEQ ID NO:186:

(i) SEQUENCE CHARACTERISTICS:
(A) LENGTH: 20 amino acids
(B) TYPE: amino acid
(C) STRANDEDNESS: single
(D) TOPOLOGY: linear ( i i ) MOLECULE TYPE: peptide ( x i ) SEQUENCE DESCRIPTION: SEQ ID NO:186:

Tyr Val Arg Cys Ser Glu Asn Gly Cys Val Gly Ser Ser Trp Glu His
1               5                   10                  15

Ser Ala Ile Ile
            20

( 2 ) INFORMATION FOR SEQ ID NO:187:

( i ) SEQUENCE CHARACTERISTICS:
  ( A ) LENGTH: 20 amino acids
  ( B ) TYPE: amino acid
  ( C ) STRANDEDNESS: single
  ( D ) TOPOLOGY: linear ( i i ) MOLECULE TYPE: peptide ( x i ) SEQUENCE DESCRIPTION: SEQ ID NO:187:

Tyr Val Arg Cys Ser Glu Gly Gly Cys Val Gly Ser Thr Trp Thr Ala
1               5                   10                  15

Ser Tyr Pro Asn
            20

( 2 ) INFORMATION FOR SEQ ID NO:188:

( i ) SEQUENCE CHARACTERISTICS:
  ( A ) LENGTH: 20 amino acids
  ( B ) TYPE: amino acid
  ( C ) STRANDEDNESS: single
  ( D ) TOPOLOGY: linear ( i i ) MOLECULE TYPE: peptide ( x i ) SEQUENCE DESCRIPTION: SEQ ID NO:188:

Phe Val Arg Cys Ser Glu Ser Gly Cys Val Gly Ser Thr Trp Ser Tyr
1               5                   10                  15

Gly Leu Ser Val
            20

( 2 ) INFORMATION FOR SEQ ID NO:189:

( i ) SEQUENCE CHARACTERISTICS:
  ( A ) LENGTH: 20 amino acids
  ( B ) TYPE: amino acid
  ( C ) STRANDEDNESS: single
  ( D ) TOPOLOGY: linear ( i i ) MOLECULE TYPE: peptide ( x i ) SEQUENCE DESCRIPTION: SEQ ID NO:189:

Tyr Val Arg Cys Ser Glu Ser Gly Cys Val Gly Ser Thr Trp Val His
1               5                   10                  15

Thr His His Leu
            20

( 2 ) INFORMATION FOR SEQ ID NO:190:

( i ) SEQUENCE CHARACTERISTICS:
  ( A ) LENGTH: 20 amino acids
  ( B ) TYPE: amino acid
  ( C ) STRANDEDNESS: single
  ( D ) TOPOLOGY: linear ( i i ) MOLECULE TYPE: peptide ( x i ) SEQUENCE DESCRIPTION: SEQ ID NO:190:

```
Tyr  Val  Arg  Cys  Ser  Glu  Ser  Gly  Cys  Val  Gly  Cys  Glu  Leu  Val  Trp
1                   5                        10                       15
Tyr  Phe  Thr  Thr
               20
```

(2) INFORMATION FOR SEQ ID NO:191:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:191:

```
Tyr  Val  Arg  Cys  Ser  Glu  Ser  Gly  Cys  Val  Gly  Ser  Thr  Trp  Asn  Gly
1                   5                        10                       15
Val  Leu  Ser  Arg
               20
```

(2) INFORMATION FOR SEQ ID NO:192:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:192:

```
Tyr  Val  Ala  Cys  Ser  Glu  Ser  Gly  Cys  Val  Ser  Val  Asp  Ser  Ser  Ala
1                   5                        10                       15
Gly  Ala  Leu  Phe
               20
```

(2) INFORMATION FOR SEQ ID NO:193:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:193:

```
Tyr  Val  Arg  Cys  Asn  Glu  Thr  Gly  Cys  Val  Gly  Ser  Ser  Trp  Ile  Ala
1                   5                        10                       15
Ala  Gly  Pro  Phe
               20
```

(2) INFORMATION FOR SEQ ID NO:194:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:194:

```
Tyr  Val  Arg  Cys  Ser  Glu  Ser  Gly  Cys  Val  Gly  Ser  Thr  Trp  Leu  Phe
1                   5                        10                       15
```

```
Asn Phe Trp Gly
           20
```

PEPTIDES THAT BIND IL-2 RECEPTORS

BACKGROUND OF THE INVENTION

1. Field of the Invention

The present invention provides peptides and compounds that bind to receptors which contain at least one of the α, β or γ IL-2 receptor subunits. The invention has application in the fields of biochemistry and medicinal chemistry. In particular, the present invention provides IL-2 inhibitors for use in the treatment of human disease.

2. Description of Related Art

Immunology has experienced rapid advances throughout the past decade, especially in the determination of the mechanisms by which the immune system is activated and regulated. Development of successful models for immunologic regulation is an important scientific objective, given the critical role of such regulation in the body's inflammatory response and in pathologic conditions such as lupus, AIDS, and cancer. The development of new techniques for organ transplantation has also created a major demand for immunosuppressive drugs to forestall foreign tissue rejection.

One area of major activity with regards to immune system regulation involves lymphokines. These substances were discovered in the mid- 1960s when Norwell noted that plant lectins were mitogenic for lymphocytes. However, it was not until a decade later, when techniques for culturing T-cells for prolonged periods became available, that interest in this area developed with the discovery that IL-2 is a central component for T-cell proliferation. This realization led to the discovery of the IL-2 receptor (IL-2R), the activation of which, by IL-2, was shown to be the signal for T-cell division (see INTERLEUKIN-2, Kendall Smith ed., pp. 1–6, Academic Press (1988), which is incorporated herein by reference).

Three classes of IL-2 receptors have been identified. The high-affinity receptor ($K_D=10^{-11}$M) contains three subunits: IL-2Rα, IL-2Rβ and IL-2Rγ. An intermediate-affinity receptor ($K_D=10^{-9}$M) comprises the IL-2Rβ and IL-2Rγ subunits. In contrast, the IL-2α subunit binds IL-2 with low affinity ($K_D=10^{-8}$M). (Minami, et al., *Ann Rev. Immunol.*, 11:245–267 (1993), which is incorporated herein by reference.)

IL-2Rα has a molecular weight of about 55 kD, but is not a constituent of resting cells. Rather, the expression of IL-2Rα is induced by a variety of factors, including antigen, phorbol esters, mitogenic lectins, TNF-α and the tax protein of HTLV-1 (Ballard, et al., THE MOLECULAR ASPECTS OF AUTOIMMUNITY, p. 227, Academic Press (1990); and Paul, PRINCIPLES OF IMMUNOLOGY (Raven Press 1992), both of which are incorporated herein by reference). IL-2Rβ is a glycoprotein having a molecular weight of about 70 kD and is a constituent of resting T and NK cell surfaces. In addition, it has been shown that the β subunit is indispensable for signal transduction (see EP 539,748 A1 to Shimamura, et al.) It has been suggested that the α subunit controls primarily association while the β subunit regulates ligand dissociation (see Ballard, et al.) The γ subunit is believed to augment binding by the β subunit as well as have a role in signal transduction. The gene coding for IL-2Rγ has been placed into a vector and successfully transfected into cells to render them capable of producing IL-2Rγ (see, Sugamura, et al., European Patent Application No. 578,932 A2, which is incorporated herein by reference). An assay for the detection of the gene and an antibody for immune response regulation based on the IL-2Rγ chain are also described by Sugamura, et al.

Because of the γ subunit's multi-faceted role in regulating the response of immune cells to stimulation, both as a signal transducer and binding agent, there have been efforts to control the immune response through blocking the IL-2/IL-2Rβ interaction. For example, EP 539,748 A1 to Shimamura, et al. describes the production of polypeptides capable of competitively binding to IL-2Rβ. These polypeptides are characterized by having about 240 residues and containing a functional antibody V-region capable of selectively inhibiting the binding of IL-2 to the β subunit. Others have focused on developing antibodies to the α subunit and IL-2 analogs (see, e.g., U.S. Pat. No. 5,229,109 to Grimm, et al.)

Recently, the γ subunit has been implicated in the regulation of IL-4, IL-7 and possibly IL-13 as well as IL-2 (see, *Science*, 262:1818 (1993); Kondo; and Russell, et al., *Science*, 262: 1880–1883 (1993), each of which is incorporated herein by reference). With respect to IL-4, the γ subunit may be a component of a heterodimer which enhances the affinity of IL-4 binding in a fashion similar to IL-2 as just described. The implication of the γ subunit in the regulation of IL-2 and IL-4 indicates that the γ subunit is a pivotal component in T and B cell development. Defective γ subunit production has been identified as a key factor in X-linked severe combined immunodeficiency disease (XSCID, commonly known as the "bubble boy disease"). IL-4 has also been implicated recently in the stimulation of B-cells and mast cells, in particular stimulating the differentiation of B-cells to produce IgE. Thus IL-4 is a promising candidate for use as an antiviral, antibacterial and anticancer drug. Additionally, IL-4 has been identified as a possible treatment for Kaposi's Sarcoma, which is considered to be the most deadly complication associated with AIDS (*Biotechnology News* 14:4–5 (Feb. 11, 1994), incorporated herein by reference). The γ subunit has also been linked to a high affinity IL-7 receptor dimer (Noguchi, et al., *Science*, 262: 1877–1880 (1993), incorporated herein by reference), further implicating this particular subunit in the regulation of thymocyte development. Also, the IL-2Rγ and IL-2Rβ subunits have been proposed as having binding affinity for the recently discovered IL-15 cytokine (*Science*, 264:965–967 (1994), incorporated herein by reference).

The availability of recombinant receptor proteins allows for the study of receptor-ligand interaction in a variety of random and semi-random peptide diversity generation systems. These systems include the "peptides on plasmids" system described in U.S. patent application Ser. No. 963,321 filed Oct. 15, 1992, which is a continuation-in-part of U.S. Pat. No. 5,270,170, the "peptides-on-phage" system described in U.S. patent application Ser. No. 718,577, filed Jun. 20, 1991, and in Cwirla et al., Aug. 1990, *Proc. Natl. Acad. Sci. USA* 87:6378–6382, the "encoded synthetic library" (ESL) system described in U.S. patent application Ser. No. 946,239, filed Sep. 16, 1992, which is a continuation-in-part of Ser. No. 762,522, filed Sep. 18, 1991, and the "Very Large Scale Immobilized Polymer Synthesis" system described in U.S. Pat. No. 5,143,854; PCT patent publication No. 90/15070, published Dec. 13, 1990; U.S. patent application Ser. No. 624,120, filed Dec. 6, 1990; Fodor et al., 15 Feb. 1991, *Science* 251:767–773; Dower and Fodor, 1991, *Ann. Rep. Med. Chem.* 26:271–180; and U.S. patent application Ser. No. 805,727, filed Dec. 6, 1991. Each of the foregoing patent applications and publications is incorporated herein by reference.

Thus, there remains a need for non-toxic compounds that bind to or otherwise interact with IL-2, IL4, IL-7 and IL-13 receptors with high affinity, both for studies of the important biological activities mediated by this receptor and for treatment of disease. The present invention provides such compounds.

SUMMARY OF THE INVENTION

The present invention provides peptides and peptidomimetics that bind to IL-2Rα, IL-2Rβ, IL-2Rγ, the αβ and βγ heterodimers and the αβγ heterotrimer. In general, compounds which bind to one subunit will bind to any combination of subunits containing that particular subunit, e.g., peptides that bind to IL-2Rβ also bind to the IL-2αβ and IL-2βγ heterodimers as well as the IL-2αβγ heterotrimer. However, not all peptides specific for the IL-2Rα subunit bind to all combinations containing the IL-2Rα subunit.

Compounds that are specific for IL-2Rβ are defined generally by the amino acid sequence $X_1X_2X_3X_4RWGDVGDLX_5X_6$ (SEQ ID NO:1), where each amino acid is denoted by its one-letter abbreviation. $X_{1-4}$ and $X_7$ may be any naturally occurring L-amino acid; $X_5$ is selected from the group consisting of V and I; and $X_6$ is selected from the group consisting of P, V, G, W, and E. In one preferred embodiment, $X_1$ is selected from the group consisting of I, G and F; $X_2$ is selected from the group consisting of S, V and P; $X_3$ is selected from the group consisting of A, Q and V; $X_4$ is selected from the group consisting of G, S and P; $X_5$ is I; $X_6$ is selected from the group consisting of P and E. An especially preferred embodiment has the sequence $X_1X_2X_3X_4RWGDVGDLX_5X_6X_7$ (SEQ ID NO:2) wherein $X_7$ is selected from the group consisting of W and L.

Additional compounds specific for IL-2Rβ are defined by the sequence $RX_8GX_9VGDX_{10}X_{11}X_{12}$ (SEQ ID NO:3), where $X_8$ is selected from the group consisting of Y and W, $X_9$ is selected from the group consisting of D and E, $X_{10}$ is selected from the group consisting of L and M, $X_{11}$ is selected from the group consisting of V, L and I, and $X_{12}$ is selected from the group P, G, V, W, E, A, M and S; $SGCGRELX_{13}WC$ (SEQ ID NO:4), where $X_{13}$ is selected from the group consisting of D and G; $WX_{14}GPGX_{15}GEX_{16}X_{17}$ (SEQ ID NO:5), where $X_{14}$ is selected from the group consisting of D, S, Y and E, $X_{15}$ is selected from the group consisting of V and L, $X_{16}$ is selected from the group consisting of Y and F, and $X_{17}$ is selected from the group consisting of F, I and M; and the sequences MDCSEAVLGELC (SEQ ID NO:6), HCLDMGCTFPVW (SEQ ID NO:7), ARSDYGLGAIWP (SEQ ID NO:8) and RACRVMPCLPDL (SEQ ID NO:9).

In still another embodiment, the present invention includes IL-2Rβ-specific sequences having the general formula $X_{18}X_{19}X_{20}X_{21}X_{22}X_{23}X_{24}X_{25}X_{26}X_{27}LC$ (SEQ ID NO:10), wherein $X_{18}$ is selected from the group consisting of M, L, T, V and I; $X_{19}$ is selected from the group consisting of D, N, G, E and S; $X_{20}$ is selected from the group consisting of C and S; $X_{21}$ is selected from the group consisting of G, S, H, R, W and Y; $X_{22}$ is any naturally occurring L-amino acid; $X_{23}$ is selected from the group consisting of A and R; $X_{24}$ is selected from the group consisting of T, A, G, V, M, I, and S; $X_{25}$ is selected from the group consisting of L, V and I; $X_{26}$ is selected from the group consisting of G and W; and $X_{27}$ is selected from the group consisting of E, Q and D. Preferred sequences have the formulae: IDCGVATVGELC (SEQ ID NO:11), IDCSEAALGELC (SEQ ID NO:12), ISCSEAGLGELC (SEQ ID NO:13), INCSEAVIGQLC (SEQ ID NO:14), IDCSQAMLGELC (SEQ ID NO:15), IDCSNAVVGQLC (SEQ ID NO:16), IDCSEAVLGELC (SEQ ID NO:17), IDCSAAGLGELC (SEQ ID NO:18), IDCSEAALGTLC (SEQ ID NO:19), LDCSNAGVGDLC (SEQ ID NO:20), LDCSIAALGELC (SEQ ID NO:21), LDCSEAVLGELC (SEQ ID NO:22), LDCSEAILGQLC (SEQ ID NO:23), LDCHLAVLGELC (SEQ ID NO:24), LDCGEAILGELC (SEQ ID NO:25), LDCSVAVLGELC (SEQ ID NO:26), LDCRDAVLGELC (SEQ ID NO:27), LDCSEAVLGHLC (SEQ ID NO:28), MDCSERALGELC (SEQ ID NO:29), MDCSQAALGDLC (SEQ ID NO:30), MDCSQAGLCELC (SEQ ID NO:31), MDCSVAVLGDLC (SEQ ID NO:32), MDCREAALGELC (SEQ ID NO:33), MDCSDAVLGDLC (SEQ ID NO:34), MDCWEAALGELC (SEQ ID NO:35), MDCHEAALGHLC (SEQ ID NO:36), MDCSEALLGELC (SEQ ID NO:37), MDCSQAVLGELC (SEQ ID NO:38), MDCYDARLGDLC (SEQ ID NO:39), MDCSIRALGELC (SEQ ID NO:40), MDSSQAALGELC (SEQ ID NO:41), TECSEAGLWELC (SEQ ID NO:42), VDCSEAVLGQLC (SEQ ID NO:43), MDCSEAVLGELC (SEQ ID NO:44), ISCSEAGLGELC (SEQ ID NO:45), MDCSERALGELC (SEQ ID NO:46), MDCSQAALGDLC (SEQ ID NO:47), and MDCSQAGLGELC (SEQ ID NO:48).

Compounds that are specific for IL-2Rα comprise core structures defined generally by the amino acid sequence $X_{28}X_{29}X_{30}CX_{31}X_{32}X_{33}GCX_{34}GSX_{35}WX_{36}X_{37}$ (SEQ ID NO:49), where $X_{28}$ and $X_{30-37}$ are any naturally occurring L-amino acid, and $X_{29}$ is selected from the group of V and R. In one preferred embodiment, $X_{28}$ is selected from the group consisting of Y, F, L and W; $X_{30}$ is selected from the group consisting of A, R and I; and $X_{35}$ is selected from the group consisting of S, N, G and T. An especially preferred embodiment is a peptide having the sequence $X_{28}X_{29}X_{30}CX_{31}X_{32}X_{33}GCX_{34}$ (SEQ ID NO:50).

In still another embodiment, the present invention includes IL-2Rα-specific sequences comprising the formula $X_{38}VRCX_{39}X_{40}X_{41}GCVGSX_{42}WX_{43}X_{44}$ (SEQ ID NO:51). Preferably, $X_{38}$ is selected from the group consisting of Y and F; $X_{39}$ is selected from the group consisting of S, G, A, N and T; $X_{40}$ is selected from the group consisting of amino acids comprising acidic side chains; $X_{41}$ is selected from the group consisting of S, T, N, D and I; $X_{42}$ is selected from the group consisting of S and T; and $X_{43}$ and $X_{44}$ are any naturally occurring L-amino acid. More preferably, $X_{40}$ is selected from the group consisting of E, V, A, D, P and L; $X_{43}$ is selected from the group consisting of N, S, V, F, G, W, T and Q; and $X_{44}$ is selected from the group consisting of A, F, L, T, W, S, I, V, Q and Y.

The present invention also includes IL-2Rα-binding peptides having the general formula $X_{45}VX_{46}X_{47}X_{48}X_{49}X_{50}GCVGSX_{51}WX_{52}X_{53}$ (SEQ ID NO:52) wherein $X_{45}$ is selected from the group consisting of Y and F; $X_{46}$ is selected from the group consisting of R, L and A; $X_{47}$ is selected from the group consisting of C and S; $X_{48}$ is selected from the group consisting of S, T and G; $X_{49}$ is selected from the group consisting of A, E, D, Q and Y; $X_{50}$ is selected from the group consisting of N, S, T, D, L, A and I; $X_{51}$ is selected from the group consisting of S, T, G and L; $X_{52}$ is selected from the group consisting of V, T, N, H, S, L and G; and $X_{53}$ is selected from the group consisting of F, Y, G, H, L, T, V, A and I.

The IL-2Rα-binding peptides disclosed herein also include those having the general sequence $X_{54}VRCX_{55}EX_{56}GCVX_{57}X_{58}X_{59}X_{60}X_{61}X_{62}X_{63}X_{64}X_{65}X_{66}$ (SEQ ID NO:53), where $X_{54}$ is Y or F; $X_{55}$ and $X_{57}$ are selected independently from the group consisting of S and G; $X_{56}$ is selected from the group consisting of S, R, I, G and N; $X_{58}$ is selected from the group consisting of S, H, C and Q; $X_{59}$ is selected from the group consisting of F, E, S, R, N, H and T; $X_{60}$ is selected from the group consisting of L, W and P; $X_{61}$ is selected from the group consisting of H, V, G, S, E, N, A and T; and $X_{62-66}$ is any naturally occurring L-amino acid. In preferred embodiments, $X_{62}$ is selected from the group consisting of S, R, P, L, M, Y, G, A, V, Q, W and T; $X_{63}$ is selected from the group consisting of Y, T, P, S, G, W, V and L; $X_{64}$ is selected from the group consisting of K, T, A, F, H, Y, W, P, L, G, and E; $X_{65}$ is selected from the group consisting of S, K, R, V, H, N, L, T, I and P; and $X_{66}$ is selected from the group consisting of A, G, P, T, S, W, I, V, L, R, D, H and N. Another preferred embodiment comprises peptides having the sequence YVRCSESGCVGX$_{58}$X$_{59}$X$_{60}$X$_{61}$X$_{62}$X$_{63}$X$_{64}$X$_{65}$X$_{66}$ (SEQ ID NO:54), wherein $X_{58}$ is selected from the group consisting of S and C; $X_{59}$ is selected from the group consisting of S and E; $X_{60}$ is selected from the group consisting of W and L; $X_{61}$ is selected from the group consisting of G and V; $X_{62}$ is selected from the group consisting of A and W; $X_{63}$ is selected from the group consisting of Y and V; $X_{64}$ is selected from the group consisting of A and F; $X_{65}$ is selected from the group consisting of S and T; and $X_{66}$ is selected from the group consisting of T and I.

The present invention also includes peptide sequences specific for IL-2Rγ, CTQEVYYSLL (SEQ ID NO:55) and CGTQEACFGLL (SEQ ID NO:56).

The present invention further includes sequences which bind to IL-2Rα having the general sequence YV$X_{67}$C$X_{68}X_{69}X_{70}$GCV$X_{71}X_{72}X_{73}X_{74}X_{75}X_{76}X_{77}X_{78}X_{79}$ $X_{80}$ (SEQ ID NO:57), wherein $X_{67}$ is selected from the group consisting of A and R; $X_{68}$ is selected from the group consisting of S and N; $X_{69}$ is selected from the group consisting of E and Q; $X_{70}$ is selected from the group consisting of S and T; $X_{71}$ is selected from the group consisting of S and G; $X_{72}$ is selected from the group consisting of S and V; and $X_{73}$ is selected from the group consisting of T, D and S; $X_{74}$ is selected from the group consisting of S and W; $X_{75}$ is selected from the group consisting of S, L and I; $X_{76}$ is selected from the group consisting of A and F; $X_{77}$ is selected from the group consisting of G, N and A; $X_{78}$ is selected from the group consisting of A, P and G; $X_{79}$ is selected from the group consisting of L, W and P; and $X_{80}$ is selected from the group consisting of F and G. Preferred sequences include YVRCSESGCVGSTWLFNPWG (SEQ ID NO:58), YVRCNETGCVGSSWIAAGPF (SEQ ID NO:59), and YVACSESGCVSVDSSAGALF (SEQ ID NO:60).

The present invention also includes sequences which bind to IL-2Rβ having the general sequence RDCS$X_{81}$A$X_{82}$LGELC (SEQ ID NO:61), wherein $X_{81}$ is V, E or D; and $X_{82}$ is V or A. Preferred sequences are RDCSVAVLGELC (SEQ ID NO:62), RDCSEARLGELC (SEQ ID NO:63), and RDCSDAVLEGLC (SEQ ID NO:64).

The present invention also provides methods for inhibiting binding to receptors containing IL-2Rα, IL-2Rβ or IL-2Rγ subunits, and methods for treating disease and disease symptoms resulting from such binding utilizing the compounds of the invention. The present invention further provides pharmaceutical compositions comprising one and more compounds of the invention and a physiologically acceptable carrier. Also included within the scope of the present invention are assays utilizing the compounds described herein and their derivatives.

DETAILED DESCRIPTION OF THE INVENTION

I. Definitions

To facilitate an understanding of the present invention, the following terms are defined below.

The term "pharmaceutically acceptable salts," as used herein, refers to the non-toxic alkali metal, alkaline earth metal, and ammonium salts commonly used in the pharmaceutical industry including the sodium, potassium, lithium, calcium, magnesium, barium, ammonium, and protamine zinc salts, which are prepared by methods well known in the art. The term also includes non-toxic acid addition salts, which are generally prepared by reacting the compounds of this invention with a suitable organic and inorganic acid. Representative salts include the hydrochloride, hydrobromide, sulfate, bisulfate, acetate, oxalate, valerate, oleate, laurate, borate, benzoate, lactate, phosphate, tosylate, citrate, maleate, fumarate, succinate, tartrate, and napsylate salts, and the like.

The term "lower alkyl," as used herein, refers to straight and branched chain alkyl groups having from 1 to 6 carbon atoms, such as methyl, ethyl, n-propyl, iso-propyl, n-butyl, tert-butyl, sec-butyl, n-pentyl, n-hexyl, 1,2-dimethylbutyl, and the like. Usually, the lower alkyl group is methyl or ethyl.

The term "lower alkoxy," as used herein, refers to straight and branched chain alkoxy groups having from 1 to 6 carbon atoms, such as methoxy, ethoxy, n-propoxy, iso-propoxy, n-butoxy, tert-butoxy, sec-butoxy, n-pentoxy, n-hexoxy, 1,2-dimethylbutoxy, and the like. Usually, the lower alkoxy group is methoxy or ethoxy.

The term "lower ester derivative," as used herein, refers to straight and branched chain alkyl ester derivatives having from 1 to 6 carbon atoms, such as methyl, ethyl, n-propyl, iso-propyl, n-butyl, tert-butyl, sec-butyl, n-pentyl, n-hexyl, 1,2-dimethylbutyl ester derivatives, and the like. Usually, the lower ester derivative is a methyl ester derivative or an ethyl ester derivative.

As used herein, the twenty naturally occurring amino acids and their abbreviations follow conventional usage (see IMMUNOLOGY—A SYNTHESIS, 2nd Edition, E. S. Golub and D. R. Gren, Eds., Sinauer Associates, Sunderland, Mass. (1991), which is incorporated herein by reference). Amino acid residues in peptides are abbreviated as follows: Phenylalanine is Phe or F; Leucine is Leu or L; Isoleucine is Ile or I; Methionine is Met or M; Norleucine is Nle; Valine is Val or V; Serine is Ser or S; Proline is Pro or P; Threonine is Thr or T; Alanine is Ala or A; Tyrosine is Tyr or Y; Histidine is His or H; Glutamine is Gln or Q; Asparagine is Asn or N; Lysine is Lys or K; Aspartic Acid is Asp or D; Glutamic Acid is Glu or E; Cysteine is Cys or C; Tryptophan is Trp or W; Arginine is Arg or R; Glycine is Gly or G, and X is any naturally occurring L-amino acid or its D-isomer. Stereoisomers (e.g., D-amino acids) of the twenty conventional amino acids, unnatural amino acids such as α,α-disubstituted amino acids, N-alkyl amino acids, lactic acid, and other unconventional amino acids may also be suitable components for polypeptides of the present invention. Examples of unconventional amino acids include: 4-hydroxyproline, O-phosphoserine, N-acetylserine, N-formylmethionine, 3-methylhistidine, 5-hydroxylysine, and other similar amino acids and imino acids (e.g., 4-hydroxyproline). In the polypeptide notation used herein, the left-hand direction is the amino terminal direction and the right-hand direction is the carboxy-terminal direction, in accordance with standard usage and convention.

As used herein, the term "receptor-binding peptide" refers to a polypeptide that binds to a predetermined receptor (e.g., a polypeptide hormone receptor) with a significant binding affinity in suitable aqueous binding conditions (e.g., physiological conditions; 1×PBS at 37° C.). Significant binding affinity typically is at least $1 \times 10^5 M^{-1}$, and usually about $1 \times 10^6 M^{-1}$. Receptor-binding peptides generally possesses a biological activity (e.g., biochemical response, specific gene expression, cytoarchitectural change) that is mediated by the predetermined receptor; in some cases, the receptor binding peptide will block a biological activity by antagonizing the effect of an agonist (e.g., the physiological ligand) for the predetermined receptor. "Biological activity" refers to a detectable change in gene expression, a biochemical pathway, cell architecture, or other detectable cell phenotype that is modulated by the predetermined receptor (e.g., the IL-2Rβ receptor subunit is required for signal transduction in immune cells, thus an IL-2Rβ-binding peptide that blocked signal transduction in a responsive cell type would be an IL-2Rβ-binding peptide having biological activity). As noted above, generally peptides that bind to any one subunit will bind to any combination of subunits containing that particular subunit. However, not all peptides specific for the IL-2Rα subunit bind to all combinations containing the IL-2Rα subunit.

As used herein, the terms "peptide" and "polypeptide" refer to macromolecules which comprise a multiplicity of amino or imino acids (or their equivalents) in peptide linkage, wherein said polypeptides may comprise or lack post-translational modifications (e.g., glycosylation, cleavage, phosphorylation, side-chain derivation, and the like).

As used herein, the terms "label" or "labeled" refers to incorporation of a detectable marker, e.g., by incorporation of a radiolabeled amino acid or attachment of biotinyl moieties to a polypeptide, wherein said attached biotinyl moieties can be detected by marked avidin (e.g., streptavidin containing a fluorescent marker or enzymatic activity that can be detected by optical or colorimetric methods). Various methods of labeling polypeptides and glycoproteins are known in the art and may be used. Examples of labels for polypeptides include, but are not limited to, the following: radioisotopes (e.g., $^3H$, $^{14}C$, $^{35}S$, $^{125}I$, and $^{131}I$), fluorescent labels (e.g., FITC, rhodamine, lanthanide phosphors), enzymatic labels (e.g., horseradish peroxidase, β-galactosidase, luciferase, alkaline phosphatase), biotinyl groups, predetermined polypeptide epitopes recognized by a secondary reporter (e.g., leucine zipper pair sequences, binding sites for secondary antibodies, metal binding domains, epitope tags). In some embodiments, labels are attached by spacer arms of various lengths to reduce potential steric hindrance.

In addition to polypeptides consisting only of naturally-occurring amino acids, peptidomimetics of the receptor-binding peptides are also provided. Peptide analogs are commonly used in the pharmaceutical industry as non-peptide drugs with properties analogous to those of the template peptide. These types of non-peptide compound are termed "peptide mimetics" or "peptidomimetics" (Fauchere, J. (1986) Adv. Drug Res. 15: 29; Veber and Freidinger (1985) TINS p.392; and Evans et al. (1987) J. Med. Chem. 30: 1229, which are incorporated herein by reference). Peptide mimetics that are structurally similar to therapeutically useful peptides may be used to produce an equivalent therapeutic or prophylactic effect. Generally, peptidomimetics are structurally similar to a paradigm polypeptide (i.e., a polypeptide that has a biological or pharmacological activity), such as naturally-occurring receptor-binding polypeptide, but have one or more peptide linkages optionally replaced by a linkage selected from the group consisting of: —CH$_2$NH—, —CH$_2$S—, —CH$_2$—CH$_2$—, —CH=CH— (cis and trans), —COCH$_2$—, —CH(OH)CH$_2$—, and —CH$_2$SO—, by methods known in the art and further described in the following references: Spatola, A. F. in CHEMISTRY AND BIOCHEMISTRY OF AMINO ACIDS, PEPTIDES, AND PROTEINS, B. Weinstein, eds., Marcel Dekker, New York, p. 267 (1983); Spatola, A. F., Vega Data (March 1983), Vol. 1, Issue 3, PEPTIDE BACKBONE MODIFICATIONS (general review); Morley, J. S., Trends Pharm Sci (1980) pp. 463–468 (general review); Hudson, D. et al., Int J Pept Prot Res (1979) 14:177–185 (—CH$_2$NH—, CH$_2$CH$_2$—); Spatola, A. F. et al., Life Sci (1986) 38:1243–1249 (—CH$_2$—S); Hann, M. M., J Chem Soc Perkin Trans I (1982) 307–314 (—CH—CH—, cis and trans); Almquist, R. G. et al., J Med Chem (1980) 23:1392–1398 (—COCH$_2$—); Jennings-White, C. et al., Tetrahedron Lett (1982) 23:2533 (—COCH$_2$—); Szelke, M. et al., European Appln. EP 45665 (1982) CA: 97:39405 (1982) (—CH(OH)CH$_2$—); Holladay, M. W. et al., Tetrahedron Lett (1983) 24:4401–4404 (—C(OH)CH$_2$—); and Hruby, V. J., Life Sci (1982) 31:189–199 (—CH$_2$—S—); each of which is incorporated herein by reference. A particularly preferred non-peptide linkage is —CH$_2$NH—. Such peptide mimetics may have significant advantages over polypeptide embodiments, including, for example: more economical production, greater chemical stability, enhanced pharmacological properties (half-life, absorption, potency, efficacy, etc.), altered specificity (e.g., a broad-spectrum of biological activities), reduced antigenicity, and others. Labeling of peptidomimetics usually involves covalent attachment of one or more labels, directly or through a spacer (e.g., an amide group), to non-interfering position(s) on the peptidomimetic that are predicted by quantitative structure-activity data and/or molecular modeling. Such non-interfering positions generally are positions that do not form direct contacts with the macromolecules(s) (e.g., immunoglobulin superfamily molecules) to which the peptidomimetic binds to produce the therapeutic effect. Derivitization (e.g., labeling) of peptidomimetics should not substantially interfere with the desired biological or pharmacological activity of the peptidomimetic. Generally, peptidomimetics of receptor-binding peptides bind to the receptor with high affirmity and possess detectable biological activity (i.e., are agonistic or antagonistic to one or more receptor-mediated phenotypic changes).

Systematic substitution of one or more amino acids of a consensus sequence with a D-amino acid of the same type (e.g., D-lysine in place of L-lysine) may be used to generate more stable peptides. In addition, constrained peptides comprising a consensus sequence or a substantially identical consensus sequence variation may be generated by methods known in the art (Rizo and Gierasch (1992) Ann. Rev. Biochem. 61: 387, incorporated herein by reference); for example, by adding internal cysteine residues capable of forming intramolecular disulfide bridges which cyclize the peptide.

II. General Methods and Compounds of the Invention

The present invention provides compounds that bind to and/or block the IL-2Rα, IL-2Rβ, IL-2Rγ receptors, the αβ and βγ heterodimers and the αβγ heterotrimer. These compounds include "lead" peptide compounds, discovered using random peptide diversity generating systems, and "derivative" compounds that have been constructed so as to have the same or similar molecular structure or shape as one or more lead compounds but that differ from the lead compound with respect to susceptibility to hydrolysis or proteolysis and/or with respect to other biological properties, such as increased affinity for, e.g., IL-2Rα, IL-2Rβ, IL-2Rγ, the αβ and βγ heterodimers and/or the αβγ heterotrimer. In general, compounds which bind to one subunit will bind to any combination of subunits containing that particular subunit, e.g., peptides that bind to IL-2Rβ also bind to the αβ and βγ heterodimers as well as the αβγ heterotrimer. However, not all peptides specific for the IL-2Rα subunit bind to all combinations containing the IL-2Rα subunit.

The random peptide diversity generating systems employed in the discovery of the lead compounds include both the "peptides-on-plasmids" and "peptides-on-phage" systems described above. The random peptides were generally designed to be twelve or more amino acid residues in length. To generate the collection of oligonucleotides encoding the random peptides, the codon motif $(NNK)_x$, where N is nucleotide A, C, G, or T (equimolar; depending on the methodology, other nucleotides can be employed), K is G or T (equimolar), and x is 12, was used to specify any one of the 32 possible codons resulting from the NNK motif: 1 for each of 12 amino acids, 2 for each of 5 amino acids, 3 for each of 3 amino acids, and only one of the three stop codons. Thus, the NNK motif encodes all of the amino acids, encodes only one stop codon, and reduces codon bias.

In the systems employed, the random peptides were presented either on the surface of a phage particle, as part of a fusion protein comprising either the pIII or the pVIII coat protein of a phage fd derivative (peptides on phage), or as a fusion protein with LacI bound to a plasmid (peptides on plasmids). The phage or plasmids, including the DNA encoding the peptides, were identified and isolated by an affinity enrichment process using immobilized IL-2Rα, IL-2Rβ, IL-2Rγ and the αβ heterodimer. The affinity enrichment process, sometimes called "panning", involves multiple rounds of incubating the phage or plasmids with immobilized receptor, collecting the phage or plasmids that bind to the receptor (along with the accompanying DNA), and producing more of the phage or plasmids (along with accompanying LacI-peptide fusion protein) collected.

After several rounds of affinity enrichment, the phage or plasmids and accompanying peptides were examined by ELISA to determine if the peptides bind specifically to the receptor. This assay was carried out in a manner similar to the procedures used in the affinity enrichment process, except that after removing unbound phage (or plasmids), the wells were typically treated with rabbit anti-phage antibody, then with alkaline phosphatase (AP)-conjugated goat anti-rabbit antibody, or with anti-LacI-AP, and then the amount of alkaline phosphatase in each well was determined by standard methods. By comparing test wells with control wells containing an unrelated receptor, one can determine whether a peptide binds to IL-2Rα (or IL-2Rβ, γ, αβ, or βγ) specifically. Peptides found to bind specifically to the receptor were then synthesized as the free peptide (no phage) and tested for binding against (1) immobilized soluble receptor, (2) receptor expressed on the surface of cells, (3) the heterotrimer form of the receptor (i.e., IL-2Rαβγ) expressed on the surface of cells and (4) the two heterodimers IL-2Rαβ and IL-2Rβγ.

The immobilized receptor used in the affinity enrichment and ELISA procedures was produced in recombinant host cells in a truncated form. This truncated receptor molecule can be produced in a variety of different forms and host cells. One useful form of receptor is constructed by expressing the protein as a soluble protein in baculovirus transformed host cells using standard methods; another useful form is constructed with a signal peptide for protein secretion and for glycophospholipid membrane anchor attachment. This form of anchor attachment is called "PIG-tailing;" see Caras and Weddell, 3 Mar. 1989, Science 243:1196-1198, and Lin et al., 10 Aug. 1990, Science 249:677-679, each of which is incorporated herein by reference. Using the PIG-tailing system, one can cleave the receptor from the surface of the cells expressing receptor (e.g., transformed Chinese hamster ovary (CHO) cells selected for high level expression of receptor with a cell sorter) with phospholipase C. The cleaved receptor still comprises a carboxy terminal sequence of amino acids, called the "HPAP tail", from the signal for membrane attachment and can be immobilized without further purification.

The recombinant receptor protein was immobilized by coating the wells of microtiter plates with an anti-HPAP tail antibody, blocking with bovine serum albumin (BSA) in PBS, and then binding recombinant, truncated receptor to the antibody. Using this procedure, one should perform the immobilization reaction in varying concentrations of the receptor to determine the optimum amount for a given preparation, because different preparations of recombinant protein often contain different amounts of the desired protein. In addition, one should ensure that the immobilizing antibody is completely blocked (with the receptor or some other blocking compound) during the affinity enrichment process. Otherwise, unblocked antibody can bind undesired phage during the affinity enrichment procedure. One can use peptides that bind to the immobilizing antibody to block unbound sites that remain after receptor immobilization to avoid this problem or one can simply immobilize the receptor directly, without the aid of an immobilizing antibody. See U.S. patent application Ser. No. 947,339, filed Sep. 18, 1992, incorporated herein by reference.

When using random peptide generation systems that allow for multivalent ligand-receptor interaction, one must recognize that the density of the immobilized receptor is an important factor in determining the affinity of the ligands that can bind to the immobilized receptor. At higher receptor densities (i.e., each anti-receptor antibody-coated well treated with 0.25 to 50.0 μg of receptor), multivalent binding is more likely to occur (if at all) than at lower receptor densities (i.e., each anti-receptor antibody-coated well treated with 0.5 to 1 ng of the receptor). If multivalent binding is occurring, then one will be more likely to isolate ligands with relatively lower affinity, unless one uses high densities of immobilized receptor to isolate derivative compounds with higher affirmity for the receptor than the lead compounds. Typically, one can identify lead compounds using a high density of immobilized receptor and then test the derivatives of the lead compounds at lower receptor densities to isolate compounds with higher affinity for the receptor than the lead compound.

Using the pVIII-based peptides on phage system, several libraries were screened to discover phages that presented lead peptides that bind to IL-2Rα, IL-2Rβ, and/or IL-2Rγ, and/or the αβ heterodimer. The phage DNA was sequenced to determine the sequence of the peptides displayed on the surface of the phages. Five leads specific to IL-2Rβ were discovered by screening pVIII-bound 10-mers against the IL-2Rαβ heterodimer: ARYGDVGSLV (SEQ ID NO:65), RWGDVGDMVV (SEQ ID NO:66), RYGEVGDLLP (SEQ ID NO:67), SGCGRELDWC (SEQ ID NO:68), and WDG-PGLGEFF (SEQ ID NO:69). All bound to the αβ heterodimer, and all were determined to be specific for the β subunit.

These peptide sequences served as the basis for the construction of other peptide libraries designed to contain a high frequency of derivatives of the lead peptides. Such libraries can be synthesized so as to favor the production of peptides that differ from the lead peptide in only a few residues. This approach involves the synthesis of an oligonucleotide with the lead peptide coding sequence, except that rather than using pure preparations of each of the four nucleoside triphosphates in the synthesis, one uses mixtures of the four nucleoside triphosphates (i.e., 55% of the "correct" nucleotide, and 15% each of the other three nucleotides is a preferred mixture for this purpose) so as to generate derivatives of the lead peptide coding sequence.

The lead peptide RWGDVGDMVV was used to form a mutagenesis library on pIII, which included mutagenesis of the original coding sequence at a frequency of 55:15:15:15; fixed-sliding libraries, such as XXXXGDMVV (SEQ ID NO:70), RWGDVXXXX (SEQ ID NO:71), and extended/mutagenized libraries, XXXXRWGDVGXXXX (SEQ ID NO:72), which were screened using standard elution conditions. These were produced in a peptides-on-phage system and tested under standard and low receptor density conditions. Screening these libraries yielded IL-2Rβ-binding peptides having the general formulae $X_1X_2X_3X_4RWGDVGDLX_5X_6$, (SEQ ID NO:1) and the corresponding 15-residue sequence $X_1X_2X_3X_4RWGDVGDLX_5X_6X_7$, (SEQ ID NO:5) where $X_{1-4}$ are any naturally occurring L-amino acid or its D-isomer, $X_5$ is selected from the group consisting of V and I and $X_6$ is selected from the group consisting of P, V, G, W, and E; and $X_7$ is W or L. More preferred are peptides wherein $X_1$ is selected from the group consisting of I, G and F; $X_2$ is selected from the group consisting of S, V and P; $X_3$ is selected from the group consisting of A, Q and V; $X_4$ is selected from the group consisting of G, S and P; $X_5$ is I; $X_6$ is selected from the group consisting of P and E.

Also uncovered were peptides having the sequence $RX_8GX_9VGDX_{10}X_{11}X_{12}$, (SEQ ID NO:3) where $X_8$ is selected from the group consisting of Y and W, $X_9$ is selected from the group consisting of D and E, $X_{10}$ is selected from the group consisting of L and M, $X_{11}$ is selected from the group consisting of V, L and I, and $X_{12}$ is selected from the group P, G, V, W, E, A, M and S. Representative peptides of both general sequences are listed in Table 1 below.

TABLE 1

| IL-2Rβ-Binding Peptides | | | |
|---|---|---|---|
| ISAGRWGDVGDLIP | (SEQ ID NO:73) | GVQSRWGDVGDLIPW | (SEQ ID NO:75) |
| FPVPRWGDVGDLIEL | (SEQ ID NO:74) | RWGDVGDLLP | (SEQ ID NO:76) |
| RWGDVGDLIG | (SEQ ID NO:77) | RWGDVGDLIP | (SEQ ID NO:84) |
| RWGDVGDLIW | (SEQ ID NO:78) | RWGDVGDLVA | (SEQ ID NO:85) |
| RWGDVGDLIG | (SEQ ID NO:77) | RWGDVGDLVE | (SEQ ID NO:86) |
| RWGDVGDLIV | (SEQ ID NO:79) | RWGDVGDLVW | (SEQ ID NO:87) |
| RWGDVGDLVS | (SEQ ID NO:80) | RWGDVGDLVG | (SEQ ID NO:88) |
| RWGDVGDLVM | (SEQ ID NO:81) | RWGDVGDLVP | (SEQ ID NO:89) |
| RWGDVGDMVE | (SEQ ID NO:82) | RWGDVGDMVV | (SEQ NO:90) |
| RYGEVGDLLP | (SEQ ID NO:83) | | |

The lead peptides SGCGRELDWC (SEQ ID NO:68), and WDGPGLGEFF (SEQ ID NO:69) described above were also mutagenized at a frequency of 70:10:10:10 to yield libraries which were screened against IL-2Rβ monomer under high-density conditions to provide preferred general sequences $SGCGRELX_{13}WC$ (SEQ ID NO:4), where $X_{13}$ is selected from the group consisting of D and G, and $WX_{14}GPGX_{15}GEX_{16}X_{17}$ (SEQ ID NO:5), where $X_{14}$ is selected from the group consisting of D, S, Y and E, $X_{15}$ is selected from the group consisting of V and L, $X_{16}$ is selected from the group consisting of Y and F, and $X_{17}$ is selected from the group consisting of F, I and M. These sequences are shown in Table 2.

TABLE 2

| IL-2Rβ-Binding Sequences | | | |
|---|---|---|---|
| SGCGRELGWC | (SEQ ID NO:91) | WSGPGLGEYM | (SEQ ID NO:95) |

TABLE 2-continued

IL-2Rβ-Binding Sequences

| | | | |
|---|---|---|---|
| WDGPGLGEFF | (SEQ ID NO:92) | WEGPGLGEYM | (SEQ ID NO:96) |
| WSGPGLGEFM | (SEQ ID NO:93) | WEGPGLGEYI | (SEQ ID NO:97) |
| WYGPGLGEYM | (SEQ ID NO:94) | | |

Additional screening of pVIII-bound 12-mers against immobilized IL-2Rβ revealed four β-specific clones: MDCSEAVLGELC (SEQ ID NO:6), HCLDMGCTFPVW (SEQ ID NO:7) (SEQ ID NO: ), ARSDYGLGAIWP (SEQ ID NO:8) and RACRVMPCLPDL (SEQ ID NO:9). An especially preferred peptide is MDCSEAVLGELC (SEQ ID NO:6), which was found capable of blocking IL-2 binding to the β-subunit, as well as being able to bind to both the αβ and βγ subunits. Notably, the free peptide MDCSEAVLGELC (SEQ ID NO:6) and IL-2 were found to be competitive against phage-born MDCSEAVLGELC (SEQ ID NO:6) with respect to binding to the two heterodimers, indicating that the binding regions on the αβ and βγ receptors for this peptide and IL-2 have common features or are identical. Significantly, MDCSEAVLGELC (SEQ ID NO:6) blocks IL-2 binding to the soluble IL-2Rαβ heterodimer with an $IC_{50}<500$ µM in a radioligand binding assay format.

A 70:10:10:10 misincorporation phagemid library on pIII based on this sequence was made and tested against IL-2Rβ under high-density conditions. Additional IL-2Rβ-specific sequences were uncovered having the general formula $X_{18}X_{19}X_{20}X_{21}X_{22}X_{23}X_{24}X_{25}X_{26}X_{27}LC$ (SEQ ID NO:10), wherein $X_{18}$ is selected from the group consisting of M, L, T, V and I; $X_{19}$ is selected from the group consisting of D, N, G E and S; $X_{20}$ is selected from the group consisting of C and S; $X_{21}$ is selected from the group consisting of G, S, H, R, W and Y; $X_{22}$ is any naturally occurring L-amino acid or its D-isomer; $X_{23}$ is selected from the group consisting of A and R; $X_{24}$ is selected from the group consisting of T, A, G, V, M, I, and S; $X_{25}$ is selected from the group consisting of L, V and I; $X_{26}$ is selected from the group consisting of G and W; and $X_{27}$ is selected from the group consisting of E, Q and D. Representative sequences based on the wild type sequence MDSCEAVLGELC (SEQ ID NO:6) are shown below in Table 3.

A preferred sequence has the formula $X_{18}X_{19}CSX_{22}X_{23}X_{24}LGX_{27}LC$ (SEQ ID NO:10), wherein $X_{18}$ is selected from the group consisting of M and I; $X_{19}$ is selected from the group consisting of D and S; $X_{22}$ is selected from the group consisting of E and Q; $X_{23}$ is selected from the group consisting of A and R; $X_{24}$ is selected from the group consisting of G and A; and $X_{27}$ is selected from the group consisting of E and D.

TABLE 3

IL-2Rβ-Binding Peptides

| | | | |
|---|---|---|---|
| IDCGVATVGELC | (SEQ ID NO:11) | IDCSEAALGELC | (SEQ ID NO:12) |
| ISCSEAGLGELC | (SEQ ID NO:13) | INCSEAVIGQLC | SEQ ID NO:14) |
| IDCSQAMLGELC | (SEQ ID NO:15) | IDCSNAVVGQLC | (SEQ ID NO:16) |
| IDCSEAVLGELC | (SEQ ID NO:17) | IDCSAAGLGELC | (SEQ ID NO:18) |
| IDCSEAALGTLC | (SEQ ID NO:19) | LDCSNAGVGDLC | (SEQ ID NO:20) |
| LDCSIAALGELC | (SEQ ID NO:21) | LDCSEAVLGELC | (SEQ ID NO:22) |
| LDCSEAILGQLC | (SEQ ID NO:23) | LDCHLAVLGELC | (SEQ ID NO:24) |
| LDCGEAILGELC | (SEQ ID NO:25) | LDCSVAVLGELC | (SEQ ID NO:26) |
| LDCRDAVLGELC | (SEQ ID NO:27) | LDCSEAVLGHLC | (SEQ ID NO:28) |
| MDCSERALGELC | (SEQ ID NO:29) | MDCSQAALGDLC | (SEQ ID NO:30) |
| MDCSQAGLCELC | (SEQ ID NO:31) | MDCSVAVLGDLC | (SEQ ID NO:32) |

TABLE 3-continued

IL-2Rβ-Binding Peptides

| | | | |
|---|---|---|---|
| MDCREAALGELC | (SEQ ID NO:33) | MDCSDAVLGDLC | (SEQ ID NO:34) |
| MDCWEAALGELC | (SEQ ID NO:35) | MDCHEAALGHLC | (SEQ ID NO:36) |
| MDCSEALLGELC | (SEQ ID NO:37) | MDCSQAVLGELC | (SEQ ID NO:38) |
| MDCYDARLGDLC | (SEQ ID NO:39) | MDCSIRALGELC | (SEQ ID NO:40) |
| MDSSQAALGELC | (SEQ ID NO:41) | TECSEAGLWELC | (SEQ ID NO:42) |
| VDCSEAVLGQLC | (SEQ ID NO:43) | IDCSEAGLGELC | (SEQ ID NO:99) |
| LDCSRASLGELC | (SEQ ID NO:115) | MDCRVAALGELC | (SEQ ID NO:100) |
| MDCSQAGLGELC | (SEQ ID NO:48) | MDCSKAALGELC | (SEQ ID NO:101) |

The αβ heterodimer was screened in the presence of each of the following peptides, ARYGDVGSLV (SEQ ID NO:65), RWGDVGDMVV (SEQ ID NO:66), RYGEVGDLLP (SEQ ID NO:67), SGCGRELDWC (SEQ ID NO:68) and WDGPGLGEFF (SEQ ID NO:69) under standard conditions. From this study two new peptides were discovered, SVRCSASGCV (SEQ ID NO:102) and EVICGTDGCW (SEQ ID NO:103), which bound specifically to IL-2Rα and blocked IL-2 binding to immobilized IL-2Rα at concentrations of 110 and 330 μM respectively. A 70:10:10:10 mutagenesis library based on the sequence of the peptide SVRCSASGCV (SEQ ID NO:102) was made on pIII and screened against IL-2Rα monomer immobilized at high- and low-receptor density. High density is defined as the maximum amount of receptor bound to anti-HPAP antibody immobilized on the ELISA plates. Low density is defined as the minimum amount of receptor bound to anti-HPAP antibody sufficient to produce a signal just above background in phage ELISA and $^{125}$I-labeled IL-2 binding assays.

The high density screen yielded 13 IL-2Rα-binding peptides, which were subjected to low-receptor-density panning with and without IL-2 elution prior to acid elution to yield seven additional IL-2Rα-specific sequences. The low density screen provided 7 additional sequences. These peptides are shown in Table 4. All of the peptides have the general sequence $X_{28}X_{29}X_{30}CX_{31}X_{32}X_{33}GCX_{34}$ (SEQ ID NO:50), where $X_{28}$ and $X_{30-34}$ are any naturally occurring L-amino acid or its D-isomer, and $X_{29}$ is V and R. In a preferred embodiment, $X_{28}$ is Y, F, L or W, $X_{30}$ is selected from the group consisting of A, R and I; and $X_{31}$ is S, T, N and G. In other preferred embodiments, $X_{32}$ is selected from the group consisting of V, A, L, E and S; $X_{33}$ is selected from the group consisting of S, I, T, N, W and D; and $X_{34}$ is selected from the group consisting of V and I.

TABLE 4

IL-2Rα-Binding Peptides

| | | | |
|---|---|---|---|
| YVACSVSGCV | (SEQ ID NO:104) | FRRCSASGCV | (SEQ ID NO:114) |
| YVICGASGCV | (SEQ ID NO:105) | LRRCSANGCV | (SEQ ID NO:116) |
| YVRCTAIGCV | (SEQ ID NO:106) | FVRCSLIGCV | (SEQ ID NO:117) |
| FVRCSATGCV | (SEQ ID NO:107) | FVRCNASGCV | (SEQ ID NO:118) |
| YVICSASGCV | (SEQ ID NO:108) | FVRCTEWGCV | (SEQ ID NO:119) |
| WVRCSASGCV | (SEQ ID NO:109) | FVRCTSDGCV | (SEQ ID NO:120) |
| FVRCSASGCV | (SEQ ID NO:110) | YVICSASGCV | (SEQ ID NO:121) |
| FVRCTASGCV | (SEQ ID NO:111) | FVRCTEWGCV | (SEQ ID NO:122) |

TABLE 4-continued

IL-2Rα-Binding Peptides

| | | | |
|---|---|---|---|
| FVRCTSDGCV | (SEQ ID NO:112) | FVRCSANGCV | (SEQ ID NO:98) |
| YVRCTASGCV | (SEQ ID NO:113) | FVRCTASGCI | (SEQ ID NO:123) |

The peptides YVICSASGCV (SEQ ID NO:105), FVRCTASGCV (SEQ ID NO:111) and YVRCTASGCV (SEQ ID NO:106), listed in Table 3 above, were the basis of a 70:10:10:10 mutagenesis library on phage having the sequence $XXX_F{}^YVRCSASGCVXXX$ (SEQ ID NOS: 124 and ) where X can be any naturally occurring L-amino acid or its D-isomer, and receptor. The library was screened using the following long- or short-wash protocols. In the long-wash method, the peptides were incubated with IL-2Rα at both high- and low-receptor densities for two hours at 4° C. This was followed by a first round of nine PBS washes, 15 minutes incubation at 4° C., a second round of nine PBS washes, 15 minutes incubation at 4° C., and a final round of nine PBS washes. In the high-density case, the final PBS wash was followed by acid elution. In the low-density case, the final PBS wash was followed by IL-2 baculovirus elution, five PBS washes and acid elution. In the short-wash protocol, the library was incubated at 4° C. for two hours at low receptor density of receptor followed by either acid elution or by IL-2-baculovirus elution, five PBS washes and acid elution. Screening with the long-wash protocol yielded peptides having the C-terminal-extended sequence $X_{28}X_{29}X_{30}CX_{31}X_{32}X_{33}GCX_{34}GSX_{35}WX_{36}X_{37}$ (SEQ ID NO:49), where $X_{28}$ and $X_{30-37}$ are any naturally occurring L-amino acid or its D-isomer, and $X_{29}$ is selected from the group consisting of V and R. Short-wash screening uncovered peptides with $X_{28}$ limited to Y, F, L and W, $X_{30}$ limited to A, R and I and $X_{31}$ limited to S, N, G and T.

A second 70:10:10:10 misincorporation pIII mutagenesis library was made from SVRCSASGCV (SEQ ID NO:12) having the general sequence $XXX_F{}^YVRCSASGCVXXX$ (SEQ ID NO:124). These peptides were screened against high- and low-density IL-2Rα conditions as described above. This screen revealed IL-2Rα-specific sequences having the general formula $X_{38}VRCX_{39}X_{40}X_{41}GCVGSX_{42}WX_{43}X_{44}$ (SEQ ID NO:51). Preferably, $X_{38}$ is selected from the group consisting of Y and F; $X_{39}$ is selected from the group consisting of S, G, A, N and T; $X_{40}$ is selected from the group consisting of amino acids comprising acidic side chains, i.e., side chains which contain one or more groups having $pK_a$s less than 7.0 (e.g., aspartic and glutamic acids); $X_{41}$ is selected from the group consisting of S, T, N, D and I; $X_{42}$ is selected from the group consisting of S and T; and $X_{43}$ and $X_{44}$ are any naturally occurring L-amino acid or its D-isomer. More preferably, $X_{40}$ is selected from the group consisting of E, V, A, D, P and L; $X_{43}$ is selected from the group consisting of N, S, V, F, G, W, T and Q; and $X_{44}$ is selected from the group consisting of A, F, L, T, W, S, I, V, Q and Y. A C-terminal $GS_T{}^SWXX$ (SEQ ID NOS: 125 and) motif was noted in the preferred sequences. This was unexpected in view of the ability of the corresponding 10-mers to bind to IL-2Rα. Specific peptide sequences are listed in Table 5 below.

TABLE 5

IL-2Rα-Binding Sequences

| | | | |
|---|---|---|---|
| YVRCSESGCVGSSWNA | (SEQ ID NO:126) | YVRCGETGCVGSTWSF | (SEQ ID NO:135) |
| FVRCSESGCVGSSWSA | (SEQ ID NO:127) | YVRCGVSGCVGSSWVL | (SEQ ID NO:136) |
| YVRCSASGCVGSSWFL | (SEQ ID NO:128) | YVRCGESGCVGSTWST | (SEQ ID NO:137) |
| YVRCSDSGCVGSTWGW | (SEQ ID NO:129) | FVRCSESGCVGSSWST | (SEQ ID NO:138) |
| YVRCSESGCVGSTWVF | (SEQ ID NO:130) | YVRCSESGCVGSSWWA | (SEQ ID NO:139) |
| YVRCSESGCVGSTWIF | (SEQ ID NO:131) | YVRCSANGCVGSSWVF | (SEQ ID NO:140) |
| YVLCALSGCVGSSWSS | (SEQ ID NO:132) | YVRCSVTGCVGSSWSI | (SEQ ID NO:141) |
| YVRCGESGCVGSTWST | (SEQ ID NO:133) | YVRCSESGCVGSSWSV | (SEQ ID NO:142) |
| YVRCSATGCVGSTWTF | (SEQ ID NO:134) | FVRCSADGCVGSSWLQ | (SEQ ID NO:143) |

TABLE 5-continued

IL-2Rα-Binding Sequences

| | | | |
|---|---|---|---|
| YVRCSADGCVGSSWFT | (SEQ ID NO:144) | FVRCSANGCVGSTWQA | (SEQ ID NO:148) |
| YVRCNPSGCVGSSWSI | (SEQ ID NO:145) | YVRCTESGCVGSTWTY | (SEQ ID NO:149) |
| YVRCSVTGCVGSSWSI | SEQ ID NO:146) | YVRCSVTGCVGSTWSV | (SEQ ID NO:150) |
| YVRCSESGCVGSSWSV | (SEQ ID NO:147) | YVRCSEIGCVGSTWSL | (SEQ ID NO:151) |

Screening of this pIII mutagenesis library was performed against low-density IL-2Rα with and without human IL-2 elution as described above. However, a change was made in the washing step which precedes the elution steps: the two 15-minute washes prior to elution (with acid or IL-2) were replaced by short washes of several minutes each. This change was made to prevent excessive losses of high-affinity sequences during the washing process. IL-2-Rα-binding peptide sequences uncovered by this technique had the general formula $X_{45}VX_{46}X_{47}X_{48}X_{49}X_{50}GCVGSX_{51}WX_{52}X_{53}$ (SEQ ID NO:52), wherein $X_{45}$ is selected from the group consisting of Y and F; $X_{46}$ is selected from the group consisting of R, L and A; $X_{47}$ is selected from the group consisting of C and S; $X_{48}$ is selected from the group consisting of S, T and G; $X_{49}$ is selected from the group consisting of A, E, D, Q and Y; $X_{50}$ is selected from the group consisting of N, S, T, D, L, A and I; $X_{51}$ is selected from the group consisting of S, T, G and L; $X_{52}$ is selected from the group consisting of V, T, N, H, S, L and G; and $X_{53}$ is selected from the group consisting of F, Y, G, H, L, T, V, A and I. Specific sequences isolated using human IL-2 elution are listed below in Table 6.

TABLE 6

IL-Rα-Binding Sequences

| | | | |
|---|---|---|---|
| YVRCSANGCVGSSWVF | (SEQ ID NO:152) | YVRCTESGCVGSTWTY | (SEQ ID NO:149) |
| YVRCSATGCVGSSWVG | (SEQ ID NO:153) | YVRCSASGCVGSSWNY | (SEQ ID NO:163) |
| FVRCSASGCVGSSWVG | (SEQ ID NO:154) | YVLCSASGCVGSLWTH | (SEQ ID NO:164) |
| YVRCSADGCVGSTWNL | (SEQ ID NO:155) | YVRCTDSGCVGSSWHL | (SEQ ID NO:165) |
| YVRSSQSGCVGSGWVL | (SEQ ID NO:156) | YVACSESGCVGSTWTT | (SEQ ID NO:166) |
| YVACSESGCVGSSWSV | (SEQ ID NO:157) | YVACSESGCVGSTWTF | (SEQ ID NO:167) |
| FVACGELGCVGSSWSI | (SEQ ID NO:158) | YVRCGAAGCVVSSWVY | (SEQ ID NO:168) |
| YVACSESGCVGSSWLA | (SEQ ID NO:159) | FVRCGASGCVGSTWGS | (SEQ ID NO:169) |
| YCRCTESGCVGSTWTY | (SEQ ID NO:160) | YVACSEIGCVGSTWSL | (SEQ ID NO:170) |
| FVRCTAIGCVGSSWSV | (SEQ ID NO:161) | YVACSESGCVGSSWTW | (SEQ ID NO:171) |
| YVRCSADGCVGSSWSA | (SEQ ID NO:162) | YVACSVSGCVGSSWSV | (SEQ ID NO:172) |
| YVRCTESGCVGSTWTY | (SEQ ID NO:149) | | |

The sequence YVRCSESGCVGSTWTT (SEQ ID NO:173) was found under acid elution conditions. A peptide related to SVRCSASGCV (SEQ ID NO:102), FVRCTASGCV (SEQ ID NO:111), and IL-2 were also found to compete for binding with respect to the α subunit in the phage ELISA format against phage-bearing FVRCTASGCV (SEQ ID NO:111), indicating that IL-2 and FVRCTASGCV have common, if not identical, binding regions on this heterodimer.

Screening was done on the pIII mutagenesis library YVRCSESGCVXXXXXXXXXX (SEQ ID NO:174) against both IL-2Rα and IL-2Rαβ heterodimer under high density and IL-2Rα under low density with long washes (two 15-minute incubations) and acid elution. Sequences determined to be specific for IL-2Rα at under high-density screening have the general sequence $X_{54}VRCX_{55}EX_{56}GCVX_{57}X_{58}X_{59}X_{60}X_{61}X_{62}X_{63}X_{64}X_{65}X_{66}$ (SEQ ID NO:53), where $X_{54}$ is Y or F; $X_{55}$ and $X_{57}$ are selected independently from the group consisting of S and G; $X_{56}$ is selected from the group consisting of S, R, I, G and N; $X_{58}$ is selected from the group consisting of S, H, C and Q; $X_{59}$ is selected from the group consisting of F, E, S, R, N, H and T; $X_{60}$ is selected from the group consisting of L, W and P; $X_{61}$ is selected from the group consisting of H, V, G, S, E, N, A and T; and $X_{62-66}$ is any naturally occurring L-amino acid or its D-isomer. In preferred embodiments, $X_{62}$ is selected from the group consisting of S, R, P, L, M, Y, G, A, V, Q, W and T; $X_{63}$ is selected from the group consisting of Y, T, P, S, G, W, V and L; $X_{64}$ is selected from the group consisting of K, T, A, F, H, Y, W, P, L, G, and E; $X_{65}$ is selected from the group consisting of S, K, R, V, H, N, L, T, I and P; and $X_{66}$ is selected from the group consisting of A, G, P, T, S, W, I, V, L, R, D, H and N.

Another preferred embodiment comprises peptides having the sequence YVRCSESGCVGX$_{58}$X$_{59}$X$_{60}$X$_{61}$X$_{62}$X$_{63}$X$_{64}$X$_{65}$X$_{66}$ (SEQ ID NO:54), wherein $X_{58}$ is selected from the group consisting of S and C; $X_{59}$ is selected from the group consisting of S and E; $X_{60}$ is selected from the group consisting of W and L; $X_{61}$ is selected from the group consisting of G and V; $X_{62}$ is selected from the group consisting of A and W; $X_{63}$ is selected from the group consisting of Y and V; $X_{64}$ is selected from the group consisting of A and F; $X_{65}$ is selected from the group consisting of S and T; and $X_{66}$ is selected from the group consisting of T and I. Specific sequences are shown in Table 7.

A pVIII library was also screened using standard conditions or receptor immobilization and elution with (1) the peptide FVRCTASGCV (SEQ ID NO:111) at 750 µM for 20 minutes or (2) with MBP-IL-2 elution. This screening resulted in sequences having the general formula YVX$_{67}$CX$_{68}$X$_{69}$X$_{70}$GCVX$_{71}$X$_{72}$X$_{73}$X$_{74}$X$_{75}$X$_{76}$X$_{77}$X$_{78}$X$_{79}$X$_{80}$ (SEQ ID NO:57), wherein $X_{67}$ is selected from the group consisting of A and R; $X_{68}$ is selected from the group consisting of S and N; $X_{69}$ is selected from the group consisting of E and Q; $X_{70}$ is selected from the group consisting of S and T; $X_{71}$ is selected from the group consisting of S and G; $X_{72}$ is selected from the group consisting of S and V; and $X_{73}$ is selected from the group consisting of T, D and S; $X_{74}$ is selected from the group consisting of S and W; $X_{75}$ is selected from the group consisting of S, L and I; $X_{76}$ is selected from the group consisting of A and F; $X_{77}$ is selected from the group consisting of G, N and A; $X_{78}$ is selected from the group consisting of A, P and G; $X_{79}$ is selected from the group consisting of L, W and P; and $X_{80}$ is selected from the group consisting of F and G. Specific sequences are described in Table 8.

TABLE 7

IL-2Rα-Binding Sequences

| | | | |
|---|---|---|---|
| YVRCSESGCVSSFWSAPWKA | (SEQ ID NO:175) | YVRCSESGCVGSSWSVSPHG | (SEQ ID NO:184) |
| YVRCSENGCVGHSWTQGLRT | (SEQ ID NO:176) | YVRCGESGCVSSSWSTMGNS | (SEQ ID NO:185) |
| YVRCSESGCVSQRPHVLEVW | (SEQ ID NO:177) | YVRCSENGCVGSSWEHSAII | (SEQ ID NO:186) |
| YVLCSERGCVGQNWAVGKLP | (SEQ ID NO:178) | YVRCSEGGCVGSTWTASYPN | (SEQ ID NO:187) |
| YVRCSEIGCVGSHWSSYGKH | (SEQ ID NO:179) | YVRCSESGCVGSSWGAVASI | (SEQ ID NO:183) |
| YVRCSENGCVGSSWGRVTLD | (SEQ ID NO:180) | FVRCSESGCVGSTWSYGLSV | (SEQ ID NO:188) |
| YVRCSESGCVGCELVWYFTT | (SEQ ID NO:181) | YVRCSESGCVGSTWNGVLSR | (SEQ ID NO:189) |
| YVRCSESGCVGSSWGAVASI | (SEQ ID NO:182) | YVRCSESGCVGCELVWYFTT | (SEQ ID NO:181) |

TABLE 8

IL-2Rα-Binding Sequences

| | | | |
|---|---|---|---|
| YVACSESGCVSVDSSAGALF | (SEQ ID NO:192) | YVRCSESGCVGSTWLFNPWG | (SEQ ID NO:194) |
| YVRCNETGCVGSSWIAAGPF | (SEQ ID NO:193) | | |

Cyclic peptides having the sequences shown in Table 9 were screened in a $^{125}$I IL-2 binding assay at low receptor density against both soluble IL-2Rα, IL-2Rα expressed on CHO cells and radiolabelled ligand with human IL-2 elution. All showed IC$_{50}$ values with respect to soluble IL-2Rα of about 300 μM. The synthetic cyclic peptide

SVRCSASGCV (SEQ. ID NO: 102)

was found to block the binding of $^{125}$I-labeled IL-2 to soluble IL-2Rα expressed on CHO cells with an IC$_{50}$ of 134 μM.

TABLE 9

Cyclic Peptides Specific for IL-2Rα

| | |
|---|---|
| YVRCSVTGCVGSSWSI | (SEQ ID NO:146) |
| YVRCSESGCVGSSWSV | (SEQ ID NO:142) |
| YVICSASGCV | (SEQ ID NO:108) |
| FVRCTASGCV | (SEQ ID NO:111) |
| SVRCSASGCV | (SEQ ID NO:102) |

It will be appreciated that generally all peptides having two cysteine residues are capable of forming intra- or inter-peptidyl disulfide bonds. Thus, the compounds of the present invention may exist in a cyclized form with an intermolecular disulfide bond, or as a dimer with an intermolecular disulfide bond. Such intra- or intermolecular disulfide bonds may be illustrated schematically as shown:

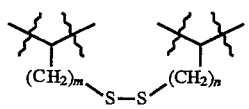

where m and n independently are 1 or 2.

Other embodiments of the present invention include analogs of these disulfide derivatives in which one of the sulfur atoms is replaced with a methylene group or similar isostere for sulfur. These analogs can be prepared from peptides wherein one of the residues to be joined is cysteine and the other residue is α-amino-γ-butyric acid through an intra- or intermolecular substitution using methods well known in the art as illustrated below:

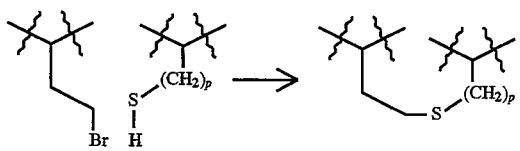

wherein p is 1 or 2. One of skill in the art will appreciate readily that the displacement just described may be conducted with other homologues of α-amino-γ-butyric acid and cysteine.

Alternatively, the amino terminus of one peptide can be capped with an α-substituted acetic acid, wherein the α substituent is a leaving group, such as an α-haloacetic acid, e.g., α-chloroacetic acid, α-bromoacetic acid, or α-iodoacetic acid. The compounds are then cyclized by inter- or intramolecular substitution by analogy to the displacement reaction just described (see, e.g., Barker, et al., J. Med. Chem., 35:2040–2048 (1992), and Or, et al., J. Org. Chem., 56:3146–3149 (1991), each of which incorporated herein by reference).

Random pVIII 10-mer and 11-mer libraries were also screened against immobilized IL-2Rγ monomer in a phage ELISA assay at high receptor density. This screening also uncovered the peptides CTQEVYYSLL and CGTQEACF-GLL which were found to bind to that subunit specifically. These peptides also bound to the βγ-subunit and competed with radiolabelled ligand. In addition, IL-2 and these peptides were found to compete with phage bearing peptides in binding to the βγ-subunit in the phage-ELISA assay, suggesting common elements or identity in the binding site of the βγ-subunit.

Peptides specific for the IL-2Rα, β and γ subunits were also discovered using a "colony lift" procedure, wherein cells were infected with DNA encoding for random amino acid sequences as described above. The phage was then allowed to grow on arabinose media to induce expression of the encoded peptides. Once a sufficient number of colonies had developed, the colonies were transferred to nitrocellulose fibers, whereupon the colonies were washed extensively and incubated at 4° C. with various tagged IL-2 receptors. The filters were washed and dried, and the tagged colonies were detected enzymatically, or by exposure to X-ray film, to identify those receptors which bound to the immobilized peptide-expressing phage particles.

Sequences which bound to IL-2Rβ have the general sequence RDCSX$_{81}$AX$_{82}$LGELC, wherein X$_{81}$ is V, E or D; and X$_{82}$ is V or A. Preferred sequences are RDCSVAVLGELC, RDCSEARLGELC (SEQ ID NO: ), and RDCSDAVLEGLC (SEQ ID NO: ).

As noted above, the peptides of the invention have also been prepared by classical methods known in the art by using standard solid phase techniques. The standard methods include exclusive solid phase synthesis, partial solid phase synthesis, fragment condensation, classical solution synthesis, and recombinant DNA technology. See, e.g., Merrifield, J. Am. Chem. Soc. 85:2149 (1963), incorporated herein by reference. On solid phase, the synthesis is typically commenced from the C-terminal end of the peptide using an α-amino protected resin. A suitable starting material can be prepared, for instance, by attaching the required α-amino acid to a chloromethylated resin, a hydroxymethyl resin, or a benzhydrylamine resin. One such chloromethylated resin is sold under the tradename BIO-BEADS SX-1 by Bio Rad Laboratories, Richmond, Calif., and the preparation of the hydroxymethyl resin is described by Bodonszky et al., Chem. Ind. (London) 38:1597 (1966). The benzhydrylamine (BHA) resin has been described by Pietta and Marshall, 1970, Chem. Commn. 650, and is commercially available from Beckman Instruments, Inc., Palo Alto, Calif., in the hydrochloride form. A particularly preferred resin is a PAL resin available from Millipore Corp., Bedford, Mass.

Thus, the compounds of the invention can be prepared by coupling an α-amino protected amino acid to the chloromethylated resin with the aid of, for example, cesium bicarbonate catalyst, according to the method described by Gisin, 1973, Helv. Chim. Acta 56:1467. After the initial coupling, the α-amino protecting group is removed by a choice of reagents including trifluoroacetic acid (TFA) or hydrochloric acid (HCl) solutions in organic solvents at room temperature.

The α-amino protecting groups are those known to be useful in the art of stepwise synthesis of peptides. Included are acyl type protecting groups (e.g. formyl, trifluoroacetyl, acetyl), aromatic urethane type protecting groups (e.g. benzyloxycarboyl (Cbz) and substituted Cbz), aliphatic urethane protecting groups, e.g. t-butyloxycarbonyl (Boc), isopropyloxycarbonyl, cyclohexyloxycarbonyl, 9-fluorenylmethoxycarbonyl (Fmoc), and alkyl type protecting groups (e.g. benzyl, triphenylmethyl). Boc and Fmoc are preferred protecting groups. The side chain protecting group remains intact during coupling and is not split off during the deprotection of the amino-terminus protecting group or during coupling. The side chain protecting group also must be removable upon the completion of the synthesis of the final peptide and under reaction conditions that will not alter the target peptide. One preferred method of includes the synthesis of the peptides on a PAL resin in combination with Fmoc protecting groups.

The side chain protecting groups for Tyr include tetrahydropyranyl, tert-butyl, trityl, benzyl, Cbz, 2-Br-Cbz, and 2,5-dichlorobenzyl. The side chain protecting groups for Asp include benzyl, 2,6-dichlorobenzyl, methyl, ethyl, and cyclohexyl. The side chain protecting groups for Thr and Ser include acetyl, benzoyl, trityl, tetrahydropyranyl, benzyl, 2,6-dichlorobenzyl, and Cbz. The side chain protecting groups for Thr and Ser is benzyl. The side chain protecting groups for Arg include nitro, tosyl (Tos), Cbz, adamantyloxycarbonyl mesitoylsulfonyl (Mts), or Boc. The side chain protecting groups for Lys include Cbz, 2-chlorobenzyloxycarbonyl (2-Cl-Cbz), 2-bromobenzyloxycarbonyl (2-BrCbz), Tos, or Boc.

After removal of the α-amino protecting group, the remaining protected amino acids are coupled stepwise in the desired order. Each protected amino acid is generally reacted in about a 3-fold excess using an appropriate carboxyl group activator such as dicyclohexylcarbodiimide (DCC) in solution, for example, in methylene chloride ($CH_2Cl_2$), dimethyl formamide (DMF) mixtures.

After the desired amino acid sequence has been completed, the desired peptide is decoupled from the resin support by treatment with a reagent such as hydrogen fluoride (HF) or TFA, which not only cleaves the peptide from the resin, but also cleaves all remaining side chain protecting groups. A preferred method of decoupling includes treatment of the resin-bound peptides with 90% TFA, optionally in the presence of scavengers such as mercaptoethanol and/or anisole. When the chloromethylated resin is used, hydrogen fluoride treatment results in the formation of the free peptide acids. When the benzhydrylamine resin is used, hydrogen fluoride treatment results directly in the free peptide amide (i.e., the C-terminus is —C(O)$NH_2$). Alternatively, when the chloromethylated resin is employed, the side chain protected peptide can be decoupled by treatment of the peptide resin with ammonia to give the desired side chain protected amide or with an alkylamine to give a side chain protected alkylamide or dialkylamide. Side chain protection is then removed in the usual fashion by treatment with hydrogen fluoride to give the free amides, alkylamides, or dialkylamides.

In preparing the esters of the invention, the resins used to prepare the peptide acids are employed, and the side chain protected peptide is cleaved with base and the appropriate alcohol, i.e., methanol. Side chain protecting groups are then removed in the usual fashion by treatment with hydrogen fluoride to obtain the desired ester. These solid phase peptide synthesis procedures are well known in the art and further described in Stewart, SOLID PHASE PEPTIDE SYNTHESES (Freeman and Co., San Francisco, 1969).

These procedures can also be used to synthesize peptides in which amino acids other than the 20 naturally occurring, genetically encoded amino acids are substituted at one, two, or more positions of any of the compounds of the invention. For instance, naphthylalanine can be substituted for tryptophan, facilitating synthesis. Other synthetic amino acids that can be substituted into the peptides of the present invention include L-hydroxypropyl, L-3,4-dihydroxyphenylalanyl, α-amino acids such as L-α-hydroxylysyl and D-α-methylalanyl, L-α-methylalanyl, β-amino acids, and isoquinolyl. D-amino acids and non-naturally occurring synthetic amino acids can also be incorporated into the peptides of the present invention.

One can also modify the amino and/or carboxy terminus of the peptide compounds of the invention to produce other compounds of the invention. Amino terminus modifications include methylating (i.e., —$NHCH_3$ or —$NH(CH_3)_2$), acetylating, adding a carbobenzoyl group, or blocking the amino terminus with any blocking group containing a carboxylate functionality defined by RCOO—, where R is selected from the group consisting of naphthyl, acridinyl, steroidyl, and similar groups. Carboxy terminus modifications include replacing the free acid with a carboxamide group or forming a cyclic lactam at the carboxy terminus to introduce structural constraints. One can also cyclize the peptides of the invention, or incorporate a desamino or descarboxy residue at the termini of the peptide, so that there is no terminal amino or carboxyl group, to decrease susceptibility to proteases or to restrict the conformation of the peptide. C-terminal functional groups of the compounds of the present invention include amide, amide lower alkyl, amide di(lower alkyl), lower alkoxy, hydroxy, and carboxy, and the lower ester derivatives thereof, and the pharmaceutically acceptable salts thereof.

One can replace the naturally occurring side chains of the 20 genetically encoded amino acids (or any L or D amino acid) with other side chains, for instance with groups such as alkyl, lower alkyl, cyclic 4-, 5-, 6-, to 7-membered alkyl, amide, amide lower alkyl, amide di(lower alkyl), lower alkoxy, hydroxy, carboxy and the lower ester derivatives thereof, and with 4-, 5-, 6-, to 7-membered hetereocyclic. In particular, proline analogs in which the ring size of the proline residue is changed from 5 members to 4, 6, or 7 members can be employed.

Cyclic groups can be saturated or unsaturated, and if unsaturated, can be aromatic or non-aromatic. Heterocyclic groups preferably contain one or more nitrogen, oxygen, and/or sulfur heteroatoms. Examples of such groups include the furazanyl, furyl, imidazolidinyl, imidazolyl, imidazolinyl, isothiazolyl, isoxazolyl, morpholinyl (e.g. morpholino), oxazolyl, piperazinyl (e.g. 1-piperazinyl), piperidyl (e.g. 1-piperidyl, piperidino), pyranyl, pyrazinyl, pyrazolidinyl, pyrazolinyl, pyrazolyl, pyridazinyl, pyridyl, pyrimidinyl, pyrrolidinyl (e.g. 1-pyrrolidinyl), pyrrolinyl, pyrrolyl, thiadiazolyl, thiazolyl, thienyl, thiomorpholinyl (e.g. thiomorpholino), and triazolyl. These heterocyclic groups can be substituted or unsubstituted. Where a group is substituted, the substituent can be alkyl, alkoxy, halogen, oxygen, or substituted or unsubstituted phenyl.

One can also readily modify peptides by phosphorylation, and other methods for making peptide derivatives of the compounds of the present invention are described in Hruby, et al., 1 Jun. 1990, *Biochem J.* 268(2):249–262, incorporated herein by reference. Thus, the peptide compounds of the invention also serve as structural models for non-peptidic compounds with similar biological activity. Those of skill in the art recognize that a variety of techniques are available for constructing compounds with the same or similar desired biological activity as the lead peptide compound but with more favorable activity than the lead with respect to solubility, stability, and susceptibility to hydrolysis and proteolysis. See Morgan and Gainor, 1989, Ann. Rep. Med. Chem. 24:243–252, incorporated herein by reference. These techniques include replacing the peptide backbone with a backbone composed of phosphonates, amidates, carbamates, sulfonamides, secondary amines, and N-methylamino acids.

The compounds of the invention are useful in vitro as unique tools for understanding the biological role of the IL-2Rα, β and γ receptors, the αβ heterodimer and the αβγ heterotrimer, in addition to the receptors for IL-4, -7 and -13. The compounds of the invention can also be used to evaluate the many factors thought to influence, and be influenced by, the receptor binding process. For example, using a microphysiometer device (available from Molecular Devices Corp., Redwood City, Calif.), which measures alterations in the acidification rate of the extracellular media in response to receptor activation, the agonist and antagonist properties of the peptides of the invention may be assayed against various receptors which include one or more of the IL-2Rα, β or γ heterodimers or heterotrimer. The present compounds are also useful in the development of other compounds that bind to IL-2Rα, β and γ receptors, the αβ and βγ heterodimers and the αβγ heterotrimer, as the present invention includes compounds that provide important SAR information that facilitate such development.

The present invention also includes a method of inhibiting binding to a receptor containing an IL-2Rα, IL-2Rβ or IL-2Rγ subunit, in which the receptor is exposed to at least one peptide of the invention in an amount effective to inhibit binding to the receptor. The compounds of the invention also will find use in treating diseases and conditions related to IL-4, IL-7 and IL-13, due at least in part to the unique role the IL-2Rγ chain plays with respect to the receptors for these interleukins. Thus, the compounds of the invention will find utility in treating such diseases as Kaposi's Sarcoma, XSCID, vital and bacterial infections and cancers.

The compounds of the invention can also be administered to warm blooded animals, including humans, to block the IL-2 binding to the receptors in vivo. Thus, the present invention encompasses methods for therapeutic treatment of immune disorders that comprise administering a compound of the invention in amounts sufficient to block the binding of IL-2 to the IL-2Rα, β and γ receptors in vivo, as well as the binding of IL-4, -7 and - 13 to their respective receptors. For example, the peptides and compounds of the invention can be administered to treat symptoms related to immunologic hypersensitivity, such as graft versus host rejection, viruses, bacterial infections, Kaposi's Sarcoma and cancer. Accordingly, the present invention includes pharmaceutical compositions comprising, as an active ingredient, at least one of the peptides or other compounds of the invention in association with a pharmaceutical carrier or diluent. The compounds of the invention can be administered by oral, parenteral (intramuscular, intraperitoneal, intravenous (IV) or subcutaneous injection), transdermal, nasal, vaginal, rectal, iontophoretic or sublingual mutes of administration and can be formulated in dosage forms appropriate for each route of administration.

In another aspect, the present invention further contemplates the attachment of various drugs, e.g., immunosuppressants, immunomodulators and anti-inflammatories, to the peptides of the invention which bind to the IL-2Rα, β and γ receptors, the αβ heterodimers and the αβγ heterotrimer. Such drugs include, but are not limited to: cyclosporin, FK506, rapamycin, azathioprine, mizoribine, amipriolse, bucillamine, ditiocarb sodium, inosine pranobex, interferon-γ, lentinan, muroctasin, platonin, procodazole, tetramisole, thymomodulin, thymopentin, and ubenimex, mesalamine, olsalazine, sulfasalazine, enfenaminc acid, etofenamate, fulfenamic acid, isonixin and the like (see, THE MERCK INDEX, 11$^{th}$ Ed., (Merck & Co. 1989), which is incorporated herein by reference). Such a strategy of drug delivery avoids many of the severe side effects associated with immunosuppressants, e.g., cyclosporin's nephrotoxicity, by targeting these drugs to cells expressing IL-2 receptors. Upon binding to the receptor, the drug will be internalized into the cell. It will be appreciated from the foregoing that drugs bound to peptides specific for the α-subunit will be preferred as the α-subunit is not expressed by cells in the resting state; thus, drugs attached to α-subunit-specific peptides will act only on activated immune cells. It will also be appreciated that preferred embodiments will include those wherein the drug is attached to the peptide through an easily hydrolyzable linkage, such as an ester, which will facilitate the release of the drug into the cell once the drug/peptide conjugate has been internalized therein.

Solid dosage forms for oral administration include capsules, tablets, pills, powders, and granules. In such solid dosage forms, the active compound is admixed with at least one inert pharmaceutically acceptable carrier such as sucrose, lactose, or starch. Such dosage forms can also comprise, as is normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration include pharmaceutically acceptable emulsions, solutions, suspensions, syrups, with the elixirs containing inert diluents commonly used in the art, such as water. Besides such inert diluents, compositions can also include adjuvants, such as wetting agents, emulsifying and suspending agents, and sweetening, flavoring, and perfuming agents.

Preparations according to this invention for parenteral administration include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms may also contain adjuvants such as preserving, wetting, emulsifying, and dispersing agents. They may be sterilized by, for example, filtration through a bacteria retaining filter, by incorporating sterilizing agents into the compositions, by irradiating the compositions, or by heating the compositions. They can also be manufactured using sterile water, or some other sterile injectable medium, immediately before use.

Compositions for rectal or vaginal administration are preferably suppositories which may contain, in addition to the active substance, excipients such as cocoa butter or a suppository wax. Compositions for nasal or sublingual administration are also prepared with standard excipients well known in the art.

The dosage of active ingredient in the compositions of this invention may be varied; however, it is necessary that the amount of the active ingredient shall be such that a suitable dosage form is obtained. The selected dosage depends upon the desired therapeutic effect, on the route of administration, and on the duration of the treatment desired. Generally dosage levels of between 0.001 to 10 mg/kg of body weight daily are administered to mammals to obtain effective receptor blocking activity.

The compounds of the invention will find a variety of uses in vitro. In one embodiment, the compounds of the invention can be used in assays as probes for determining the expression of one or more IL-2 receptor subunits, their heterodimers, or the heterotrimer, on the surfaces of cells. Such an assay is useful for determining whether the cells have been exposed to antigen or the degree of cellular immune response. The compounds of the invention may also be used in affinity chromatography to isolate one more IL-2, IL-4, IL-7 or IL-13 receptor components or cells expressing such components. The compounds are also useful as competitive inhibitors in assays to screen for new IL-2, IL-4, IL-7, and IL-13 receptor blockers. In such assay embodiments, the compounds of the invention may include one or more labels, e.g., radioactive labels such as $^{125}$I, chromophoric labels such as FITC or biotinyl groups. The compounds may also include spacers or linkers in cases where the compounds are to be attached to a support, such as column.

Typically when the compounds of the invention are used to assay for the expression of one or more IL-2 receptor subunits on cells, the cells under study will be exposed to the compounds for a period sufficient for the compounds to bind to the receptor(s) expressed on the cell surface. The cells are then separated from the non-bound compounds and unreacted cells, e.g., by affinity chromatography or the use of a cell sorter, to identify whether binding of the compounds to the receptor has occurred. In one preferred embodiment, one or more of the compounds of the invention are bound to a solid substrate in known locations, such as described in U.S. Pat. No. 5,183,854 to Pirrung, et al. The substrate is then exposed to the cells which have been labeled using standard methods for a time sufficient to allow binding to occur between the compounds and expressed receptors. The unbound materials are removed and the positions of the bound cells are determined to identify the compound(s) which bind to the cell receptor(s). For example, cells labeled with antibodies carrying fluorescent markers, such as FITC, are reacted with one or more compounds of the invention bound to a substrate at known locations. The unreacted cells are then washed away, and light at a wavelength appropriate to cause fluorescence is shined on the substrate and the fluorescence is recorded. The positions of fluorescence on the substrate indicate those compounds which have bound to the cells, thereby indicating which receptor subunit(s) is expressed on the cell surface. It will be appreciated that by attaching compounds which bind to the individual subunits, their heterodimers, and the heterotrimer at known locations on the substrate, the entire range of receptor expression can be determined in a single experiment As can be appreciated from the disclosure above, the present invention has a wide variety of applications. It will be seen that the invention provides peptides which bind to the IL-2Rα, IL-2Rβ and IL-2Rγ, receptor subunits, the αβ heterodimer and the IL-2Rαβγ heterotrimer. Thus, it will be appreciated that the present invention provides substances which may be used to treat disease conditions in which activation and regulation of the immune system is a consideration. The invention also has utility in assays for identifying activated immune cells and as drug delivery vehicles.

Although certain embodiments and examples have been used to describe the invention, it will be apparent to those skilled in the art that changes may be made to those embodiments and examples without departing from the scope or spirit of the invention.

We claim:

1. A peptide that binds to IL-2Rβ, said peptide comprising the sequence $X_{18}X_{19}CSX_{22}X_{23}X_{24}LGX_{27}LC$ (SEQ ID NO:10) wherein:
   $X_{18}$ is selected from the group consisting of I and M;
   $X_{19}$ is selected from the group consisting of D and S;
   $X_{22}$ is selected from the group consisting of E and Q;
   $X_{23}$ is selected from the group consisting of A and R;
   $X_{24}$ is selected from the group consisting of A and G; and
   $X_{27}$ is selected from the group consisting of E and D.

2. A peptide that binds to IL-2R β, said peptide comprising a sequence selected from the group consisting of: Ile Asp Cys Gly Val Ala Thr Val Gly Glu Leu Cys (SEQ ID NO:11); Ile Asp Cys Ser Glu Ala Ala Leu Gly Glu Leu Cys (SEQ ID NO:12); Ile Ser Cys Ser Glu Ala Gly Leu Gly Glu Leu Cys (SEQ ID NO:13); Ile Asn Cys Ser Glu Ala Val Ile Gly Gln Leu Cys (SEQ ID NO:14); Ile Asp Cys Ser Gln Ala Met Leu Gly Glu Leu Cys (SEQ ID NO:15); Ile Asp Cys Ser Asn Ala Val Val Gly Gln Leu Cys (SEQ ID NO:16); Ile Asp Cys Ser Glu Ala Val Leu Gly Glu Leu Cys (SEQ ID NO:17); Ile Asp Cys Ser Ala Ala Gly Leu Gly Glu Leu Cys (SEQ. ID NO:18); Leu Asp Cys Ser Asn Ala Gly Val Gly Asp Leu Cys (SEQ ID NO:20); Leu Asp Cys Ser Ile Ala Ala Leu Gly Glu Leu Cys (SEQ ID NO:21); Leu Asp Cys Ser Glu Ala Val Leu Gly Glu Leu Cys (SEQ ID NO:22); Leu Asp Cys Ser Glu Ala Ile Leu Gly Gln Leu Cys (SEQ ID NO:23); Leu Asp Cys His Leu Ala Val Leu Gly Glu Leu Cys (SEQ ID NO:24); Leu Asp Cys Gly Glu Ala Ile Leu Gly Glu Leu Cys (SEQ ID NO:25); Leu Asp Cys Ser Val Ala Val Leu Gly Glu Leu Cys (SEQ ID NO:26); Leu Asp Cys Arg Asp Ala Val Leu Gly Glu Leu Cys (SEQ ID NO:27); Met Asp Cys Ser Glu Arg Ala Leu Gly Glu Leu Cys (SEQ ID NO:29); Met Asp Cys Ser Gln Ala Ala Leu Gly Asp Leu Cys (SEQ ID NO:30; Met Asp Cys Ser Val Ala Val Leu Gly Asp Leu Cys (SEQ ID NO:32); Met Asp Cys Arg Glu Ala Ala Leu Gly Glu Leu Cys (SEQ ID NO:33); Met Asp Cys Ser Asp Ala Val Leu Gly Asp Leu Cys (SEQ ID NO:34); Met Asp Cys Trp Glu Ala Ala Leu Gly Glu Leu Cys (SEQ ID NO:35); Met Asp Cys Ser Gln Ala Val Leu Gly Glu Leu Cys (SEQ ID NO:38); Met Asp Cys Ser Ile Arg Ala Leu Gly Glu Leu Cys (SEQ ID NO:40); Met Asp Ser Ser Gln Ala Ala Leu Gly Glu Leu Cys (SEQ ID NO:41); Thr Glu Cys Ser Glu Ala Gly Leu Trp Glu Leu Cys (SEQ ID NO:42); Val Asp Cys Ser Glu Ala Val Leu Gly Gln Leu Cys (SEQ ID NO:43); Met Asp Cys Ser Glu Ala Val Leu Gly Glu Leu Cys (SEQ ID NO:44); and Met Asp Cys Ser Gln Ala Gly Leu Gly Glu Leu Cys (SEQ ID NO:45).

3. The peptide of claim 2 comprising the sequence

Ile Asp Cys Gly Val Ala Thr Val Gly Glu Leu Cys (SEQ ID NO:11).

4. The peptide of claim 2 comprising the sequence

Ile Asp Cys Ser Gln Ala Ala Leu Gly Glu Leu Cys (SEQ ID NO:12).

5. The peptide of claim 2 comprising the sequence

Ile Ser Cys Ser Glu Ala Gly Leu Gly Glu Leu Cys (SEQ ID NO:13).

6. The peptide of claim 2 comprising the sequence

Ile Asn Cys Ser Glu Ala Val Ile Gly Gln Leu Cys (SEQ ID NO:14).

7. The peptide of claim 2 comprising the sequence

Ile Asp Cys Ser Gln Ala Met Leu Gly Glu Leu Cys (SEQ ID NO:15).

8. The peptide of claim 2 comprising the sequence

Ile Asp Cys Ser Asn Ala Val Val Gly Gln Leu Cys (SEQ ID NO:16).

9. The peptide of claim 2 comprising the sequence

Ile Asp Cys Ser Glu Ala Val Leu Gly Glu Leu Cys (SEQ ID NO:17).

10. The peptide of claim 2 comprising the sequence

Ile Asp Cys Ser Ala Ala Gly Leu Gly Glu Leu Cys (SEQ ID NO:18).

11. The peptide of claim 2 comprising the sequence

Leu Asp Cys Ser Asn Ala Gly Val Gly Asp Leu Cys (SEQ ID NO:20).

12. The peptide of claim 2 comprising the sequence

Leu Asp Cys Ser Ile Ala Ala Leu Gly Glu Leu Cys (SEQ ID NO:21).

13. The peptide of claim 2 comprising the sequence

Leu Asp Cys Ser Glu Ala Val Leu Gly Glu Leu Cys (SEQ ID NO:22).

14. The peptide of claim 2 comprising the sequence

Leu Asp Cys Ser Glu Ala Ile Leu Gly Gln Leu Cys (SEQ ID NO:23).

15. The peptide of claim 2 comprising the sequence

Leu Asp Cys His Leu Ala Val Leu Gly Glu Leu Cys (SEQ ID NO:24).

16. The peptide of claim 2 comprising the sequence

Leu Asp Cys Gly Glu Ala Ile Leu Gly Glu Leu Cys (SEQ ID NO:25).

17. The peptide of claim 2 comprising the sequence

Leu Asp Cys Ser Val Ala Val Leu Gly Glu Leu Cys (SEQ ID NO:26).

18. The peptide of claim 2 comprising the sequence

Leu Asp Cys Arg Asp Ala Val Leu Gly Glu Leu Cys (SEQ ID NO:27).

19. The peptide of claim 2 comprising the sequence

Met Asp Cys Ser Glu Arg Ala Leu Gly Glu Leu Cys (SEQ ID NO:29).

20. The peptide of claim 2 comprising the sequence

Met Asp Cys Ser Gln Ala Ala Leu Gly Asp Leu Cys (SEQ ID NO:30).

21. The peptide of claim 2 comprising the sequence

Met Asp Cys Ser Val Ala Val Leu Gly Asp Leu Cys (SEQ ID NO:32).

22. The peptide of claim 2 comprising the sequence

Met Asp Cys Arg Glu Ala Ala Leu Gly Glu Leu Cys (SEQ ID NO:33).

23. The peptide of claim 2 comprising the sequence

Met Asp Cys Ser Asp Ala Val Leu Gly Asp Leu Cys (SEQ ID NO:34).

24. The peptide of claim 2 comprising the sequence

Met Asp Cys Trp Glu Ala Ala Leu Gly Glu Leu Cys (SEQ ID NO:35).

25. The peptide of claim 2 comprising the sequence

Met Asp Cys Ser Gln Ala Val Leu Gly Glu Leu Cys (SEQ ID NO:38).

26. The peptide of claim 2 comprising the sequence

Met Asp Cys Ser Ile Arg Ala Leu Gly Glu Leu Cys (SEQ ID NO:40).

27. The peptide of claim 2 comprising the sequence

Met Asp Ser Ser Gln Ala Ala Leu Gly Glu Leu Cys (SEQ ID NO:41).

28. The peptide of claim 2 comprising the sequence Thr Glu Cys Ser Glu Ala Gly Leu Trp Glu Leu Cys (SEQ ID NO:42).

29. The peptide of claim 2 comprising the sequence Val Asp Cys Ser Glu Ala Val Leu Gly Gln Leu Cys (SEQ ID NO:43).

30. The peptide of claim 2 comprising the sequence Met Asp Cys Ser Glu Ala Val Leu Gly Glu Leu Cys (SEQ ID NO:44).

31. The peptide of claim 2 comprising the sequence Met Asp Cys Ser Gln Ala Gly Leu Gly Glu Leu Cys (SEQ ID NO:45).

32. A peptide that binds to IL-2R β, said peptide comprising a sequence Ile Asp Cys Ser Glu Ala Ala Leu Gly Thr Leu Cys (SEQ ID NO:19.

33. A peptide that binds to IL-2R β, said peptide comprising a sequence Leu Asp Cys Ser Glu Ala Val Leu Gly His Leu Cys (SEQ ID NO:28).

34. A peptide that binds to IL-2R β, said peptide comprising a sequence; Met Asp Cys Ser Gln Ala Gly Leu Cys Glu Leu Cys (SEQ ID NO:31).

35. A peptide that binds to IL-2R β, said peptide comprising a sequence Met Asp Cys His Glu Ala Ala Leu Gly His Leu Cys (SEQ ID NO:36).

36. A peptide that binds to IL-2R β, said peptide comprising a sequence Met Asp Cys Ser Glu Ala Leu Leu Gly Glu Leu Cys (SEQ ID NO:37).

37. A peptide that binds to IL-2R β, said peptide comprising a sequence Met Asp Cys Tyr Asp Ala Arg Leu Gly Asp Leu Cys (SEQ ID NO:39).

* * * * *